(12) United States Patent
Batiste

(10) Patent No.: US 11,547,545 B2
(45) Date of Patent: Jan. 10, 2023

(54) INFUSION FILTER AND METHOD FOR PERFORMING THROMBOLYSIS

(71) Applicant: Stanley Batiste, Granite Bay, CA (US)

(72) Inventor: Stanley Batiste, Granite Bay, CA (US)

( * ) Notice: Subject to any disclaimer, the term of this patent is extended or adjusted under 35 U.S.C. 154(b) by 521 days.

(21) Appl. No.: 16/512,155

(22) Filed: Jul. 15, 2019

(65) Prior Publication Data
US 2019/0336265 A1   Nov. 7, 2019

Related U.S. Application Data

(60) Division of application No. 15/463,991, filed on Mar. 20, 2017, now abandoned, which is a continuation-in-part of application No. 14/819,258, filed on Aug. 5, 2015, now abandoned, which is a continuation-in-part of application No. 12/012,136, filed on Jan. 30, 2008, now Pat. No. 9,387,062.

(60) Provisional application No. 62/310,456, filed on Mar. 18, 2016, provisional application No. 60/898,939, filed on Jan. 31, 2007.

(51) Int. Cl.
*A61F 2/01* (2006.01)
*A61M 25/00* (2006.01)
*A61M 39/10* (2006.01)
*A61B 17/22* (2006.01)

(52) U.S. Cl.
CPC ............. *A61F 2/01* (2013.01); *A61M 25/007* (2013.01); *A61M 25/0074* (2013.01); *A61M 25/0097* (2013.01); *A61M 39/10* (2013.01); *A61B 2017/22084* (2013.01); *A61F 2/011* (2020.05); *A61F 2002/016* (2013.01); *A61F 2230/0006* (2013.01); *A61F 2230/0091* (2013.01); *A61F 2230/0093* (2013.01); *A61F 2250/0059* (2013.01); *A61F 2250/0067* (2013.01); *A61M 2025/0057* (2013.01)

(58) Field of Classification Search
CPC .. A61B 2017/22084; A61F 2/01; A61F 2/011; A61F 2002/016; A61F 2230/0006; A61F 2230/0091; A61F 2230/0093; A61F 2250/0059; A61F 2250/0067; A61M 25/007; A61M 25/0074; A61M 25/0097; A61M 39/10; A61M 2025/0057
See application file for complete search history.

(56) References Cited

U.S. PATENT DOCUMENTS

| | | |
|---|---|---|
| 3,840,017 A | 10/1974 | Violante |
| 4,494,531 A | 1/1985 | Gianturco |
| 4,793,348 A | 12/1988 | Palmaz |
| 5,108,418 A | 4/1992 | Lefebvre |

(Continued)

*Primary Examiner* — Jocelin C Tanner
(74) *Attorney, Agent, or Firm* — Weide & Miller, Ltd.

(57) ABSTRACT

An infusion filter design combines a fluid infusion device and a blood filtration device that filter blood during a thrombolysis procedure while allowing for complete filter removal on procedure completion. In one embodiment, a wire comprises a proximal, non-infusible length that extends partially outside of the patient and within the vein. The wire further comprises an infusible length distally from the non-infusible length that is extends within the vein so as to be placed at the section of the vein requiring medication. The wire also comprises a distal filter component at a distal end of the wire that is employed to filter the blood in the event that during the period that clot is dissolved it migrates toward the central circulation.

5 Claims, 19 Drawing Sheets

(56) References Cited

U.S. PATENT DOCUMENTS

| | | | |
|---|---|---|---|
| 5,129,910 A | 7/1992 | Phan | |
| 5,188,616 A | 2/1993 | Nadal | |
| 5,256,146 A * | 10/1993 | Ensminger | A61M 25/04 |
| | | | 604/104 |
| 5,375,612 A | 12/1994 | Cottenceau et al. | |
| 5,415,630 A | 5/1995 | Gory | |
| 5,531,788 A | 7/1996 | Dibie | |
| 5,549,626 A | 8/1996 | Miller | |
| 5,624,396 A * | 4/1997 | McNamara | A61B 17/22 |
| | | | 604/264 |
| 5,707,389 A | 1/1998 | Louw et al. | |
| 5,893,869 A | 4/1999 | Barnhart | |
| 5,895,398 A * | 4/1999 | Wensel | A61B 17/22 |
| | | | 606/159 |
| 6,007,558 A | 12/1999 | Ravenscroft et al. | |
| 6,059,825 A | 5/2000 | Hobbs et al. | |
| 6,267,777 B1 | 7/2001 | Bosma et al. | |
| 6,402,736 B1 * | 6/2002 | Brown | A61M 25/0017 |
| | | | 604/264 |
| 6,558,404 B2 | 5/2003 | Tsukernik | |
| 6,589,263 B1 | 7/2003 | Hopkins | |
| 6,929,633 B2 * | 8/2005 | Evans | A61B 17/320758 |
| | | | 604/509 |
| 7,131,979 B2 | 11/2006 | DiCarlo | |
| 2001/0011181 A1 | 8/2001 | DiMatteo | |
| 2001/0039450 A1 | 11/2001 | Pavcnik et al. | |
| 2002/0010481 A1 | 1/2002 | Jayaraman | |
| 2002/0116024 A1 | 8/2002 | Goldberg et al. | |
| 2002/0138094 A1 * | 9/2002 | Borillo | A61F 2/013 |
| | | | 606/200 |
| 2002/0138097 A1 | 9/2002 | Ostrovsky et al. | |
| 2003/0018354 A1 | 1/2003 | Roth | |
| 2003/0097094 A1 * | 5/2003 | Ouriel | A61F 2/013 |
| | | | 604/93.01 |
| 2003/0135264 A1 | 7/2003 | Whalen et al. | |
| 2003/0208227 A1 | 11/2003 | Thomas | |
| 2004/0034383 A1 | 2/2004 | Belson | |
| 2004/0059290 A1 * | 3/2004 | Palasis | A61M 25/104 |
| | | | 604/102.01 |
| 2004/0158274 A1 | 8/2004 | WasDyke | |
| 2004/0193209 A1 | 9/2004 | Pavcnik et al. | |
| 2005/0107739 A1 * | 5/2005 | Palma | A61M 25/04 |
| | | | 604/104 |
| 2005/0119522 A1 | 6/2005 | Okada | |
| 2005/0131451 A1 | 6/2005 | Kleshinski et al. | |
| 2006/0212127 A1 | 9/2006 | Karabey et al. | |
| 2006/0229668 A1 | 10/2006 | Prestezog et al. | |
| 2007/0088382 A1 | 4/2007 | Bei | |
| 2007/0112372 A1 | 5/2007 | Sosnowski et al. | |
| 2007/0270901 A1 | 11/2007 | Shimon | |
| 2008/0159771 A1 | 7/2008 | Sakabe | |
| 2009/0005803 A1 | 1/2009 | Batiste | |
| 2009/0306703 A1 | 12/2009 | Kashkarov et al. | |
| 2011/0106135 A1 | 5/2011 | Thompson | |
| 2017/0119516 A1 | 5/2017 | Batiste | |

\* cited by examiner

INFUSION FILTER AND METHOD FOR PERFORMING THROMBOLYSIS

CROSS REFERENCE TO RELATED APPLICATIONS

This application claims priority to and the benefit of the following applications: U.S. Provisional Application No. 62/310,456 which was filed on Mar. 18, 2016 titled INFUSION FILTER DESIGN and is a divisional application from U.S. patent application Ser. No. 15/463,991 filed on Mar. 20, 2017 titled INFUSION FILTER AND METHOD FOR PERFORMING THROMBOLYSIS, which is a continuation in part of U.S. patent application Ser. No. 14/819,258 filed on Aug. 5, 2015 titled INTRAVENOUS FILTER WITH GUIDEWIRE AND CATHETER ACCESS GUIDE, which application is a continuation in part of U.S. patent application Ser. No. 12/012,136 filed on Jan. 30, 2008 titled IMPROVED INTRAVENOUS DEEP VEIN THROMBOSIS FILTER AND METHOD OF FILTER PLACEMENT, which claims priority to U.S. Provisional Patent Application No. 60/898,939 filed on Jan. 31, 2007 titled IMPROVED INTRAVENOUS DEEP VEIN THROMBOSIS FILTER AND METHOD OF FILTER PLACEMENT.

BACKGROUND

1. Field

The disclosed embodiments relate to vascular filters and, in particular to surgically implanted vascular filters which capture blood clots to prevent the clots from migrating to other regions of the circulatory system.

2. Related Art

Deep vein thrombosis (DVT) is a common problem and causes significant morbidity and mortality in the United States and throughout the world. DVT is the formation of a blood clot within a deep vein, predominantly in the legs. These blood clots typically occur due to slow or reduced blood flow through the deep veins such as when the patient cannot ambulate or otherwise efficiently circulate their blood. Another cause of inefficient circulation may be due to structural damage to the veins resulting from general trauma or surgical procedures. Additionally, a blood clot may form in a deep vein due to a particular medical condition or a propensity for the patient to have a hypercoaguability state. For example, a woman on birth control who smokes has an increased risk of forming blood clots and is thus predisposed to DVT.

The result and clinical significance of DVT is when the clot breaks free from its location in the deep vein of the leg. The clot travels through the circulatory system and may eventually lodge in a location that is adverse to the patient's health. For example, the clot may dislodge from a location in the deep vein of the patient's leg and migrate through the heart and come to rest in the patient's lung causing a pulmonary embolism (PE) resulting in the restricted circulation of blood in the lungs. PE may cause sudden death for the patient. As many as 600,000 cases of clinically significant Pulmonary Embolus occur and result in approximately 200,000 deaths annually in the United States.

DVT & PE are currently prevented in several ways including anticoagulation therapy, thrombectomy, thrombolysis and inferior vena cava filter (IVC filter) placement. Anticoagulation therapy utilizes various medications that reduce the patient's propensity for forming blood clots. However, this form of therapy has the disadvantage that due to the patient's inability to form blood clots (due to the medication), there is an increased risk of excessive bleeding should the patient become injured, sustain surgical complications, or develop internal hemorrhaging.

Thrombectomy is a procedure generally performed for treatment of a PE, in which a blood clot is extracted from the vein using a surgical procedure or by way of an intravenous catheter and a mechanical suction device. This form of treatment is risky and technically very difficult because the catheter has to be steered or navigated to a specific location in order to extract the clot. Additionally, during a thrombectomy there is an increased risk of causing vascular damage due to the surgical procedure and use of various mechanical devices.

Thrombolysis is a medical technique that is performed for treatment of a PE, in which various medicines are infused into the region of the clot that subsequently causes the clot to dissolve. This form of treatment has the disadvantage that the medication may cause bleeding at other sites such as within the brain. For example, if a patient has previously had a minute non-clinical stroke, the medication used in a thrombolysis may cause a previously healed vessel to bleed within the patient's head.

IVC filter placement is usually conducted by surgically installing a filter in a large bore vein (such as the inferior vena cava) in the patient's upper abdomen. The IVC filter is placed using a large bore catheter (Introducer Catheter) introduced into the patient from the patient's jugular vein and steered to the inferior vena cava for delivery of the filter. Typically, a removable IVC filter is utilized based on FDA recommendations to remove the IVC filter once protection from PE is no longer needed. In the case where a removable filter is utilized, additional complications arise when the filter must be removed.

The removable IVC filter is generally placed for a time period of a several weeks to a few months to prevent internal vascular scaring. However, removal of the IVC filter is technically challenging and requires large bore access. In practice, the removable IVC filter is captured by first accessing a large bore vein, such as the jugular vein, using a large bore catheter to approach the filter, capturing the tip of the filter using a "snaring device" that is deployed through the large bore catheter, then pulling the filter into the catheter, and then the large bore catheter (with the filter therein) is removed from the patient. This procedure is very challenging, and requires increased patient recovery time.

Current IVC filter placement has several disadvantages such as increased costs, requires the use of special surgical procedures such as fluoroscopy or cardiology labs, requires a team (lab technician, nurse, and physician) of medical professionals, and requires a second substantially difficult surgical procedure for filter removal. Additionally, the IVC filter placement procedure requires that the patient's coagulation status be sufficient to withstand the surgical procedure. For example, if the patient has medical condition (liver failure) or is on medications that prevents their blood from clotting (i.e., using anticoagulation therapy) there is a substantial risk of excessive bleeding during the procedure. Also, existing IVC filter placement procedures are of questionable practicality for preventative placement because of the intrusive surgical procedures that must be performed to place the filter. Correspondingly, the risks (particularly filter removal) must be balanced between the need for the filter and the patient's ability to endure the surgical procedure.

Other complications may also arise from existing IVC filters. For example, despite FDA recommendations, the retrieval rate of IVC filters is very low given the complexity of the procedure to remove the filters. When the filters remain in the body, there is the possibility of filter fracturing and migrating into other parts of the body. Further, the filter may perforate the wall of the vein, and may even perforate into adjoining tissues or organs.

As a result, there is a need in the art for a vascular filter that is inexpensive, facilitates placement by a physician at a convenient patient location (bedside), allows non-intrusive removal that can be performed at any location by either a physician or trained technician while having minimal recovery time and eliminating the need to determine the coagulation status of the patient. The method and vascular filter described herein enables a physician to place and remove the filter with minimal physical intrusion and at the same time reducing risk of procedural complications for the patient.

SUMMARY

To overcome the drawbacks of the prior art and provide additional benefits and features, a vascular filter and method of filter placement is disclosed. In one embodiment, the vascular filter includes a dispensing needle releasably attached to a syringe and a filter wire dispenser. Generally, the needle has two ends, a delivery end and a coupling end. The delivery end is placed within a vein and allows filter wire to be implanted into the vein. The coupling end allows the needle to be releasably connected to a filter wire dispenser or syringe.

The filter wire dispenser stores a length of filter wire which is configured to coil upon deployment from the delivery end of the needle into a vein. The filter wire dispenser may store the filter wire as a spool or linearly, and includes a guide tube sized to insert into the needle. The guide tube is used to guide the filter wire from the dispenser into the needle.

The filter wire may be configured to coil upon deployment in a number of ways. One way is to put residual stresses, surface tensions, or both into the filter wire such that, once deployed, the filter wire will coil into a predetermined shape as defined by the stresses and surface tensions in the filter wire. The filter wire may be configured to coil into a vortex type, nested, or tangled web shape as desired. In addition, the filter wire of some embodiments may have a flexible tip to better prevent damage to the interior walls of a vein.

Once deployed a portion of the filter wire may be left protruding from the patient to allow the filter to be fixed in position. The protruding portion of the filter wire may be secured to a fixation device attached to the patient's skin. In one or more embodiments, the fixation device may have a portion configured to engage and secure the filter wire such as a protrusion.

The vascular filter, in one embodiment, is implanted by accessing a vein with a needle, attaching a filter wire dispenser storing a length of filter wire to the needle, and advancing the filter wire through the needle such that the filter wire exits the delivery end of the needle. In one or more embodiments, the filter wire has two ends, a first end and a second end. In one embodiment the first end of the filter wire exits the dispenser first. As the filter wire exits the needle into the vein, it begins to coil, as described above, to form a vascular filter.

Once the vascular filter is fully deployed the needle may be removed. In one or more embodiments, a portion of the filter wire is left protruding out of the patient so that it may be secured to a fixation device which generally covers the exist passage of the filter wire.

In some embodiments, proper access to a vein may be verified prior to implanting the filter. One way to verify that the needle is accurately located in a vein is to attach a syringe to the needle and draw blood from the vein to confirm the needle is indeed properly within the vein. The needle is improperly placed if no blood can be drawn. Once verified, the syringe may be removed from the needle while leaving the needle in the vein. A filter wire dispenser may then be attached and the filter wire implanted subsequently.

The vascular filter may be removed when desired or when no longer needed. In one embodiment, the vascular filter is removed by removing the filter wire from its associated fixation device and drawing the filter wire out of the patient. As the filter wire is drawn out of the patient, the filter wire unwinds itself so that it may be easily removed.

In one embodiment, a vascular filter system as described herein is provided with medication infusion capability. In such an embodiment, the filter wire is configured to coil within or around the filter wire dispenser and further configured for coiled deployment from the filter wire dispenser to a patient, the filter wire comprising an open first end connected to a hub assembly. The filter wire includes an inner lumen within the filter wire in fluid communication with the open first end. The filter wire also includes a perforated section and a non-perforated section. Two or more infusion ports are in the perforated section such that the two or more infusion ports are in fluid communication with the inner lumen of the filter wire. A hub assembly is at the open first end such that the hub assembly is configured to surround at least a portion of the non-perforated section of the filter wire and selectively open and close the inner lumen to control the flow of medication into the perforated portion of the filter wire.

In one configuration, the infusion ports are holes in the perforated section of the filter wire which establish the inner lumen in fluid communication with the blood stream. The hub assembly may comprise a luer lock. In one embodiment, the hub assembly is configured to mate with a syringe to accept an administration of medication into the inner lumen of the filter wire.

Also disclosed is a vascular filter system that includes a length of filter wire having a first end and a second end. In this embodiment, the length further includes a non-perforated section at the first end with an opening at the first end that is part of an inner passageway within the filter wire. A perforated section connects the non-perforated section and the second end such that the perforated section is configured to coil to form a filter upon deployment from the delivery end of the dispensing needle. Also part of this embodiment are two or more perforations in the perforated section that are in fluid communication with the inner lumen. A hub assembly is releasable connected near the first end of the filter wire and is configured to selective open and close the inner lumen.

In one variation the vascular filter system further comprises an antithrombogenic on at least an outer surface of the perforated section. The portion of the filter wire that is within the hub assembly may be resilient.

In further embodiments, an infusion filter design is provided. The infusion filter design is a unique solution to the problem of DVT and PE management by lessening time and financial cost while increasing procedural efficiencies, decreasing the number of procedures and improving patient care.

The new infusion filter design is unique in that it combines a means of providing blood filtration during the procedure with complete filter removal of the filter on procedure completion. Some embodiments comprise the ability for medication infusion and simultaneous blood filtration. In one embodiment, a wire comprises a proximal, non-infusible length that extends partially outside of the patient and within the vein. The wire further comprises an infusible length distally from non-infusible length that is extends within the vein so as to be placed at the section of the vein requiring medication. The wire also comprises a distal filter component at a distal end of the wire that is employed to filter the blood in the event that during the period that clot is dissolved it migrates toward the central circulation. The filter component can be a helix shape, a vortex shape, a nested shape, and a tangled web shape. This infusion wire filter can be place using a catheter which the infusion filter wire is advanced through, deployed and the catheter pulled back. Once the clot is removed the filter and wire can be removed.

In another embodiment, the device incorporates two components: a wire with a distal filter and an infusion catheter. The wire with the distal filter is constructed with a non-infusible wire over the entire length with the distal filter tip. The distal filter tip can be made of a helix shape, a vortex shape, a nested shape, and a tangled web shape and may oppose or not oppose the inner vessel wall. The second component is an infusion catheter which is composed of a single lumen catheter with numerous perforations in the wall throughout its mid and distal length. The perforations are tiny holes which allow medication to infuse outward from the inner lumen into the desired vessel. Assembled, the wire is advanced through the infusion catheter and the filter component is deployed beyond the distal catheter tip with the whole device within the desired vessel. This configuration allows for infusion and blood filtration simultaneously which can then be removed upon completion of the procedure.

In these embodiments, the filter can either oppose or not oppose the vessel wall (float within the vessel).

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The components in the figures are not necessarily to scale, emphasis instead being placed upon illustrating the principles of the invention. In the figures, like reference numerals designate corresponding parts throughout the different views.

DETAILED DESCRIPTION OF EMBODIMENTS

In the following description, numerous specific details are set forth in order to provide a more thorough description of the present invention. It will be apparent, however, to one skilled in the art, that the present invention may be practiced without these specific details. In other instances, well-known features have not been described in detail so as not to obscure the invention.

One of the primary concerns regarding deep vein thrombosis (DVT) is that should the thrombosis (blood clot)

dislodge from the original location, the clot may travel to another region of the circulatory system and cause injury and or death to the subject. For example, if a DVT dislodges it may migrate through the heart and eventually re-lodge in the lung of the subject, thus causing a pulmonary embolism (PE) which prevents adequate circulation and respiration, and can cause sudden death. By placing an intravenous filter in the common femoral vein, the blood clot is captured and prevented from migrating to vulnerable regions of the circulatory system. The filter may be placed in any vein or at any location such that the filter can capture a clot prior to causing damage to the patient. The term vein and vessel are used and defined interchangeably herein.

Figure 1:
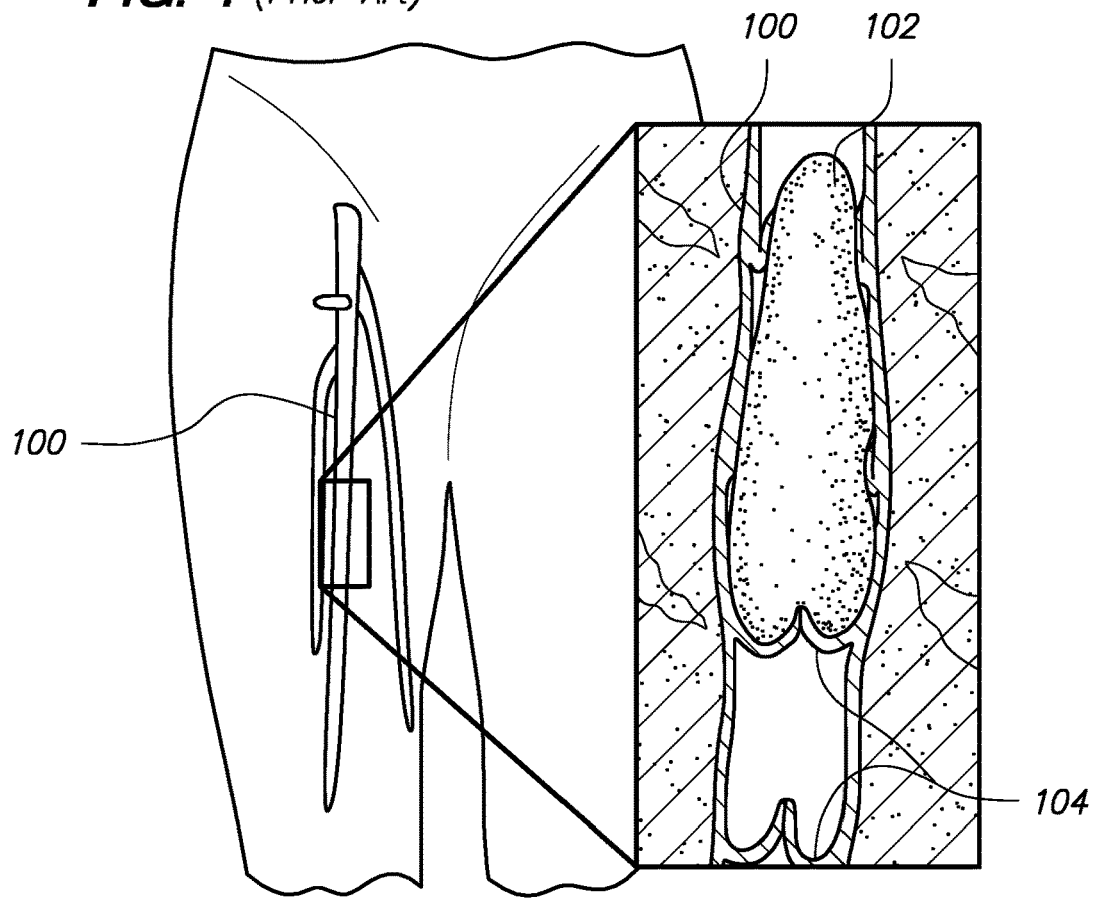
FIG. 1 illustrates a typical blood clot lodged within a femoral vein.

Referring now to the drawings, FIG. 1 illustrates a typical DVT where the common femoral vein 100 has a blood clot 102 lodged therein. As the blood clot 102 is formed there is reduced blood flow through the common femoral vein 100 because the blood clot begins to obstruct the fluid pathway. The reduced blood flow produces an environment that facilitates clot formation. In particular, as the blood flow is reduced, blood begins to coagulate in the chambers of the vascular valves 104, and, as a result, the blood clot 102 increases in size.

Figure 2:
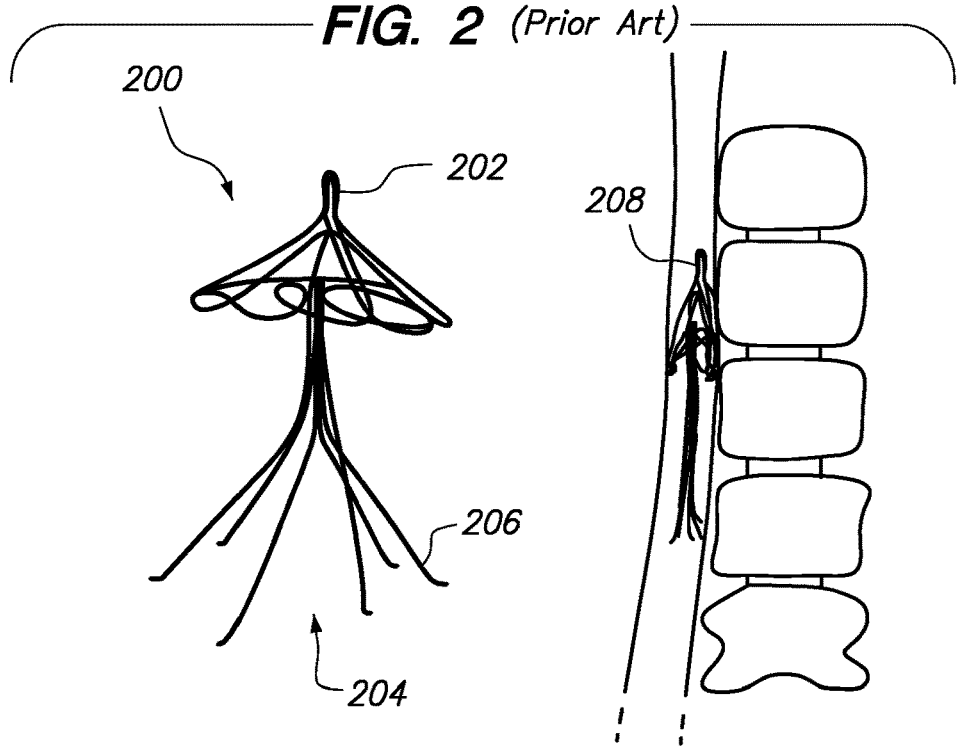
FIG. 2 illustrates an existing inferior vena cava filter and the proximate location of the filter in the upper abdomen.

FIG. 2 illustrates a known inferior vena cava vascular filter that is surgically implanted into the patient's upper abdomen. This inferior vena cava filter (IVC filter) 200 is commonly deployed using a large bore catheter and access to a large bore vein such as the inferior vena cava. The IVC filter 200 has a first end 202 and a second end 204 where the second end comprises a plurality of individual wire components 206. In the proximity diagram of FIG. 2, an IVC filter 200 is shown within the inferior vena cava at location 208 in the upper abdomen of a patient.

Figure 3:
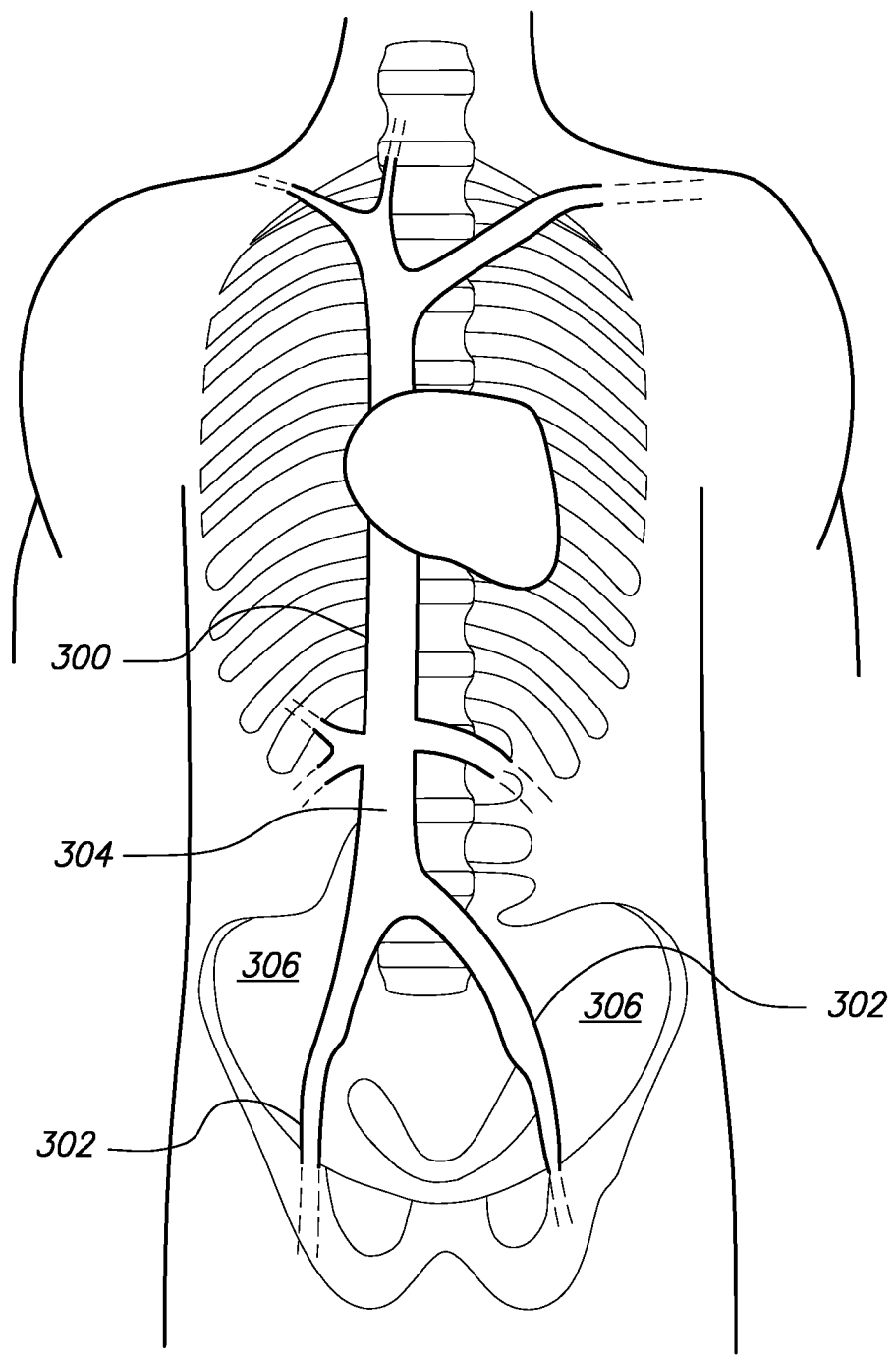
FIG. 3 illustrates the inferior vena cava and the two femoral veins.

FIG. 3 illustrates the inferior vena cava 300 and two common femoral veins 302 branching off the inferior vena cava. In the known use of intravenous filters such as the IVC filter discussed above, it is common to place the IVC filter within the inferior vena cava 300 at location 304 in the upper abdomen.

As stated above, placement of an IVC filter within the inferior vena cava 300 is expensive, requires special surgical procedures, requires imaging from a radiology or cardiology suite to ensure correct placement with the inferior vena cava, and is a substantially difficult and complicated surgery. In addition, known IVC filters must be placed in a large bore vein, and the placement surgery itself poses a significant risk in patients with conditions that prevent proper blood clotting.

The vascular filter in the disclosed embodiments has several advantages over known filters. In contrast to the above, the vascular filter of the disclosed embodiments may be placed within one of the common femoral veins 302. In addition, the vascular filter may be placed at any other location in the body which is suited to capture or retain blood clots to prevent the clots from migrating to more critical areas. The vascular filter may be placed "blind" without imaging guidance from an expensive radiology or cardiology suite. Furthermore, the vascular filter may be placed in the common femoral vein 302 at hip level which is an area routinely used for catheter and other line access. Use of this common access area is another advantage in that such use of a commonly accessed area tends to reduce complexity and risk during placement as it is a well-known access area.

Though placement at hip level has advantages, placement at hip level may not be ideal in all patients and thus the vascular filter may also be placed in other areas. For example, in one embodiment, the filter may be placed in the groin region 306 of the patient. It is contemplated that the vascular filter may be placed where it is best able to capture a dislodged blood clot and that more than one filter may be placed to ensure that any dislodged blood clots are captured. For example, in one embodiment the vascular filter may be placed in both of the common femoral veins 302 should the patient's medical condition require filtration of both legs. In other embodiments, additional vascular filters may be placed as well.

Placement of the vascular filter begins by accessing a common femoral vein 302. Though the following description describes an embodiment of the present invention where the vascular filter is placed within a common femoral vein 302, the vascular filter may be similarly placed in other veins where dislodged blood clots may be captured as necessary.

Figure 4:
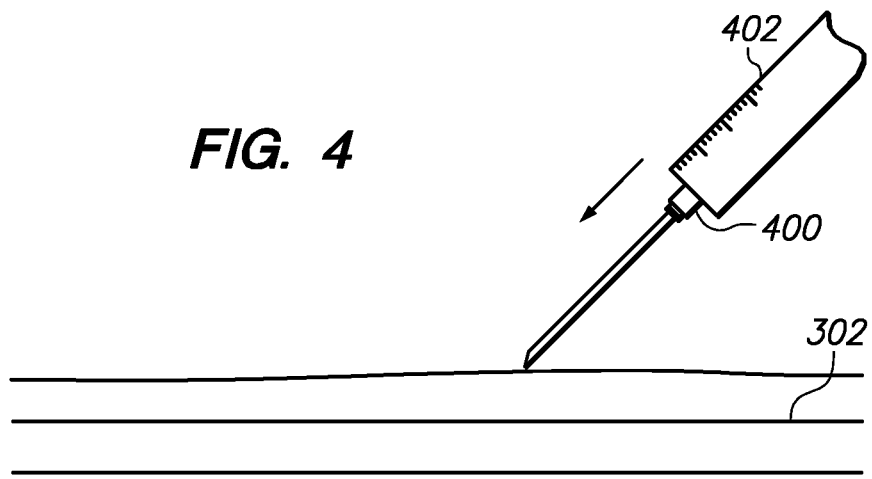
FIG. 4 illustrates a common femoral vein prior to access by a needle and syringe assembly.
Figure 5:
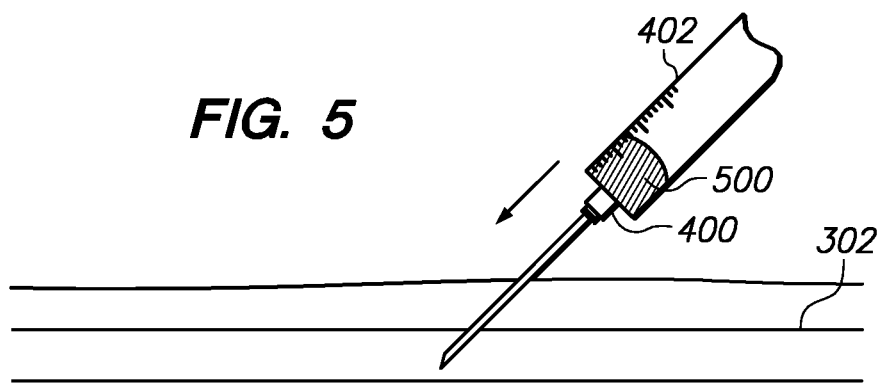
FIG. 5 illustrates actual needle and syringe assembly access into the common femoral vein.

FIGS. 4 and 5 illustrate a common femoral vein 302 accessed by a dispensing needle 400 and syringe 402 assembly. In one or more embodiments, the needle 400 has a first or delivery end through which a vascular filter is implanted in a patient, and a second or coupling end at which a syringe or filter dispenser may be attached. Notably, the coupling end in one or more embodiments may be configured to permit releasable attachment of the needle 400 as described further below.

Generally, proper access to the common femoral vein 302 may be verified by syringe aspiration (drawing blood from the vein into the body of the syringe) and is visually confirmed by blood return 500 into the syringe. In other embodiments, elements other than a syringe may be utilized including, but not limited to a single hollow large bore needle of which the blood can be seen flowing out of without syringe aspiration.

Figure 6:
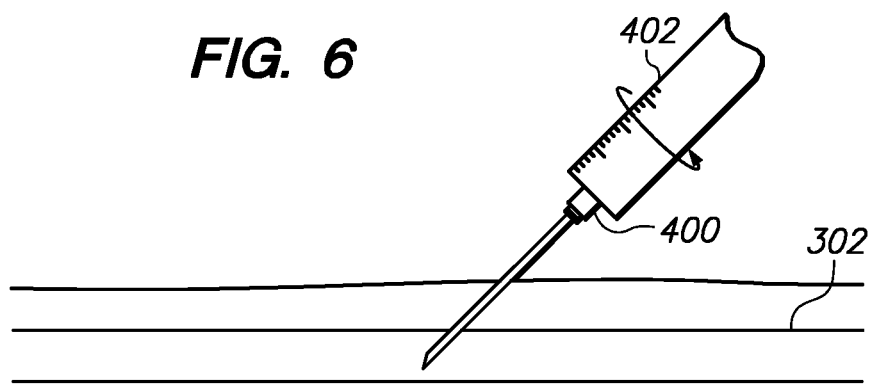
FIG. 6 illustrates removal of the syringe.

As illustrated in FIG. 6, the syringe 402 may be disengaged or removed from the needle 400 without removing the needle from the common femoral vein 302. In one or more embodiments, proper access to the common femoral vein 302 may be confirmed prior to disengaging the syringe 402 by inspecting the syringe for blood return. Such blood return confirms that the needle 400 is within a vein.

It is noted that disengagement or removal of the syringe 402 from the needle 400 may occur in various ways and that the syringe is releasably attached to the needle. For example, the syringe 402 may be fitted with a bayonet type of locking mechanism that retains the needle 400 within the end of the syringe. In addition, any other type of mechanism in addition to or other than a bayonet type locking mechanism may be utilized including but not limited to a manufactured threaded coupling system with "male and female" thread components. The locking mechanism may be any type of configuration that releasably retains the needle in the syringe and because these mechanisms are well known in the art they will not be described in detail so as not to obscure the present invention.

Figure 7:
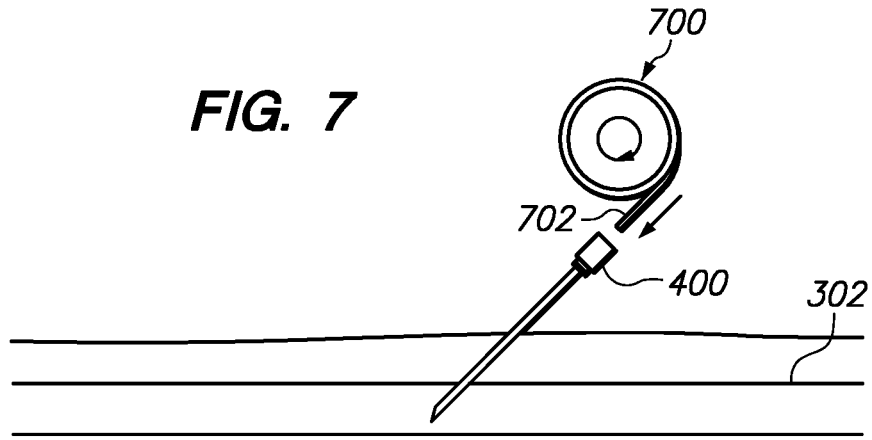
FIG. 7 illustrates attachment of the filter dispenser to the needle.

Attachment of the vascular filter dispenser 700 to the needle 400 is illustrated in FIG. 7. In one embodiment, the vascular filter dispenser 700 is a spool device that is configured to house and dispense filter wire housed within the dispenser. The vascular filter dispenser 700 is fitted with a guide tube 702 that facilitates the deployment of the filter wire from the dispenser through the needle 400 and into the common femoral vein 302. It is contemplated that the end of the guide tube 702 be sized for operative insertion into the inner diameter of the needle 400. The guide tube 702 provides a smooth transition for the filter wire during the deployment process as the wire leaves the filter dispenser 700 and enters the needle 400. In some embodiments, filter means other than a wire may be utilized such as but not limited to monofilament strand or other materials with reformable properties. These structures may be pre-formed or shaped and/or configured at the time of use.

Figure 8:
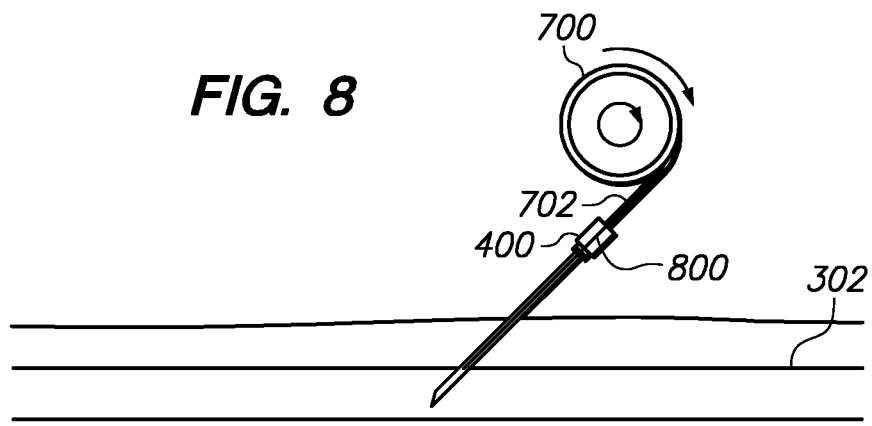
FIGS. 8, 9, 10, and 11 illustrate deployment of the vascular filter.

Reference is now made to FIGS. 8 through 11 individually and in combination for illustrating the deployment of the vascular filter. As shown in FIG. 8, a needle 400 and a vascular filter dispenser 700 are coupled together, and the filter dispenser is actuated such that the filter wire 800 is fed from the dispenser through the needle and into the common femoral vein 302. In one embodiment, the filter dispenser 700 is actuated by a rotational movement of the dispenser so that the filter wire 800 is un-coiled and fed down the guide tube 702 and into the needle 400. It is contemplated that the filter dispenser 700 may comprise a user-rotatable wheel or knob in one or more embodiments. When rotated, the knob un-coils the filter wire 800 and feeds the wire 800 down the guide tube 702. The knob may un-coil the filter wire 800 through physical contact with the filter wire. However, it is contemplated that there may be an attached reel which is actuated by rotational movement of knob. Other embodiments of the filter dispenser 700 are contemplated such as a linear dispenser by which the filter wire is translated down the length of the dispenser and into the needle.

Figure 9:
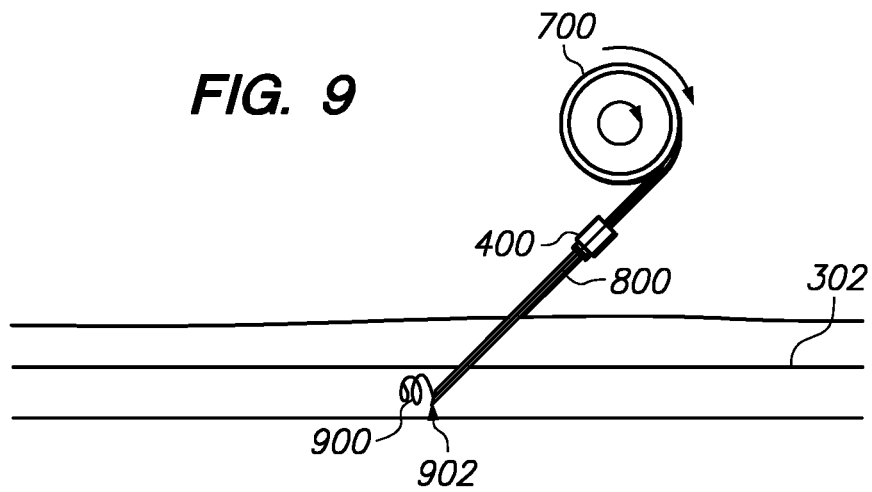

As best illustrated in FIG. 9, as the filter wire 800 traverses down the needle 400 it remains substantially straight. However, when the filter wire 800 exits the end 902 of the needle 400, the filter wire begins to form a coil 900 within the common femoral vein 302. The filter wire coils due to residual stresses of the wire and the preformed shape memory imparted into the wire during the manufacturing process.

In one or more embodiments, the filter wire 800 has a first and a second end and is preferably fabricated from a suitable material such as titanium, Nitinol, or monofilament strand, to name a few. The filter wire 800 may also be fabricated from a polymer as well. The wire may be similar to known wires commonly used in the medical industry and, in one or more embodiments, may range in diameter from 0.015-0.035 of an inch. Additionally, the filter wire 800 may be treated with a compound that prevents clot formation on the wire such as a Heparin anticoagulation coating. The wire may comprise a mesh form or may be constructed of metal, plastic or a combination thereof or any other material. In addition, the filter wire 800 may have a very flexible tip at its first end to reduce the possibility of damaging the inside wall of a vein when the filter wire is implanted.

In one embodiment, an important characteristic of the filter wire 800 is that the wire be preformed to have residual stresses and/or surface tensions such that the wire will automatically coil once advanced beyond the delivery needle end 902. For example, the filter wire may be fabricated so that the surface tension along the length of the wire causes the wire to naturally coil unless otherwise constrained. In this way, the filter wire 800 may be housed or stored in one dispenser configuration and upon proper deployment; the filter wire would coil into a predetermined shape. In another embodiment, the filter wire may be preformed to take any various shapes that will achieve the goals set forth herein. For example, the filter wire may be preformed to have a vortex shape (coils of increasing/decreasing diameter) once deployed. Other embodiments may provide filter wire that is preformed to have a nesting or tangled web shape.

Figure 10:
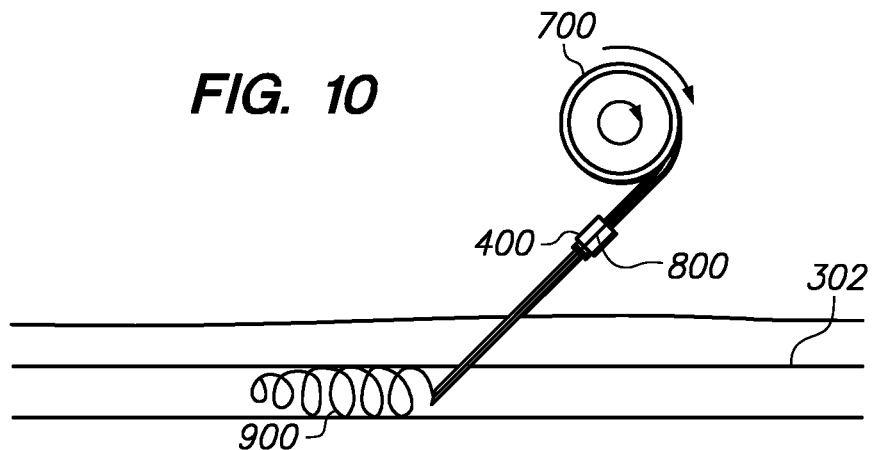
Figure 11:
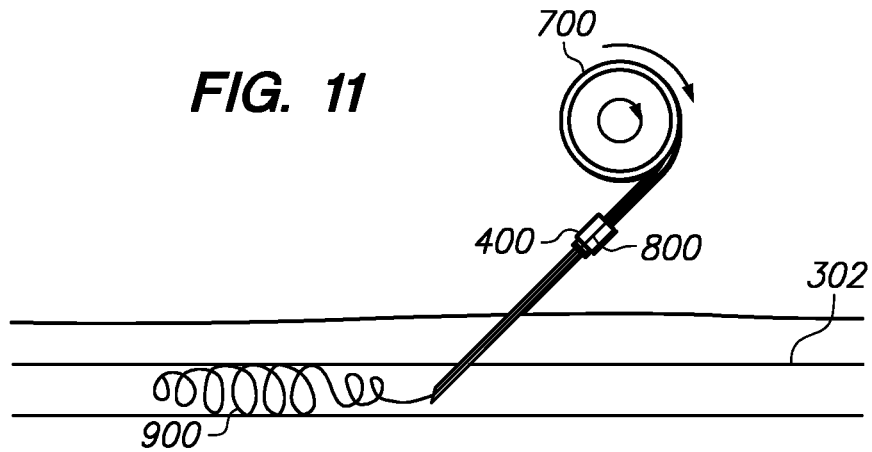

As illustrated in FIGS. 10 and 11, as the filter wire 800 is advanced into the common femoral vein 302, the coil 900 becomes larger and longer such that a substantial coil of wire is formed within the vein. As a result, the coil 900 becomes a partial flow restriction within the common femoral vein 302 capable of capturing and retaining a blood clot therein.

Figure 12:
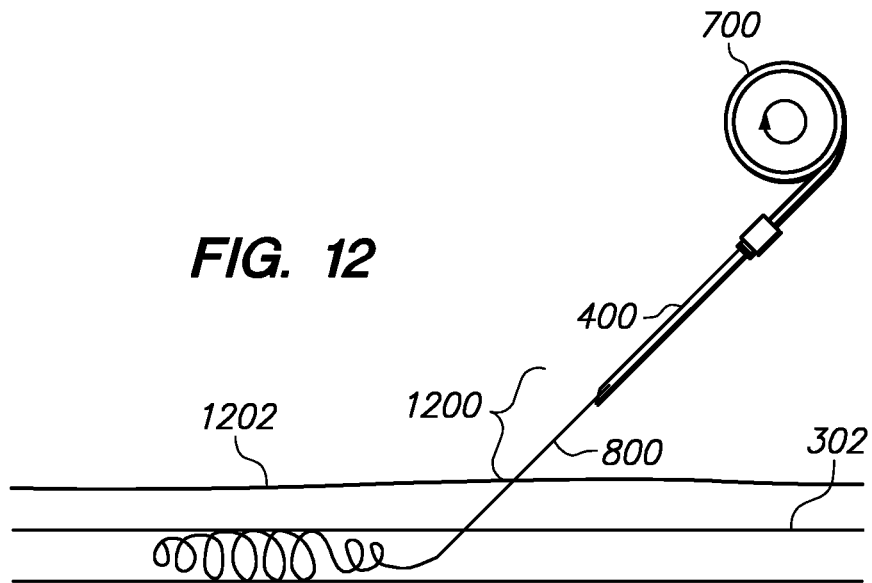
FIGS. 12 and 13 illustrate removal of the filter dispenser and needle.
Figure 13:
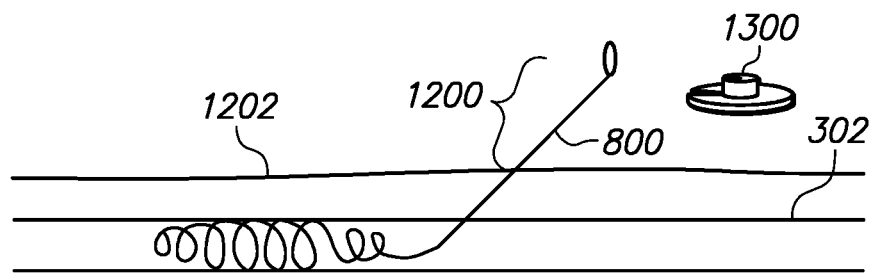
Figure 14:
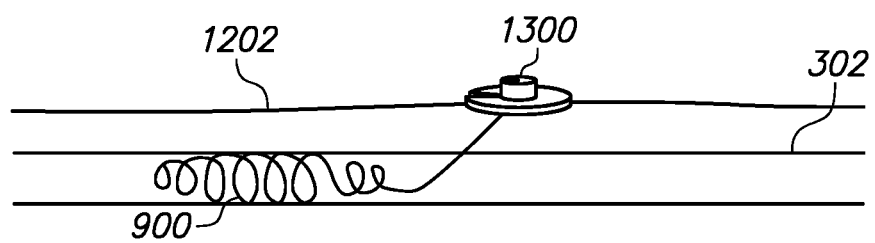
FIG. 14 illustrates retention of the filter wire to the patient's leg.

In FIG. 12, the filter wire 800 has been deployed and the filter dispenser 700 and delivery needle 400 are retracted from the subject's common femoral vein 302. As the dispenser 700 and needle 400 are removed, a portion 1200 of the filter wire 800 may be left protruding from the subject's skin surface 1202 so that it may be secured to a fixation device 1300 (FIG. 13) to prevent the filter wire 800 from moving within the vein. As illustrated in FIGS. 13 and 14, a portion 1200 of the filter wire 800 is intentionally left protruding from the subject's skin surface 1202 so that it may be looped and subsequently attached to a fixation device 1300. The fixation device 1300 is then secured using a medical dressing to the subject's skin 1202 and may cover the filter wire's exit. It is contemplated that types of fixation devices 1300 other than those illustrated in the figures may be used, and that in other embodiments the protruding portion 1200 of the filter wire 800 may be attached in other ways such as by tying or adhering the filter wire to the fixation device.

Figure 15:
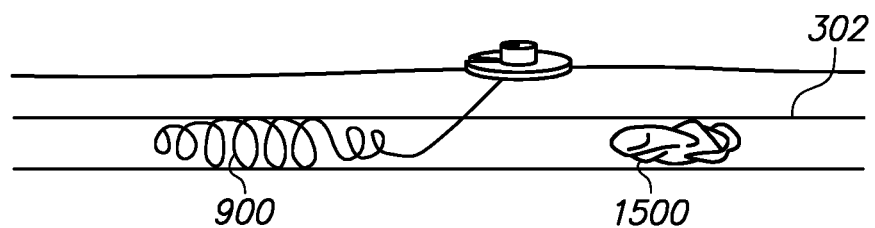
FIG. 15 illustrates a blood clot approaching the deployed vascular filter.
Figure 16:
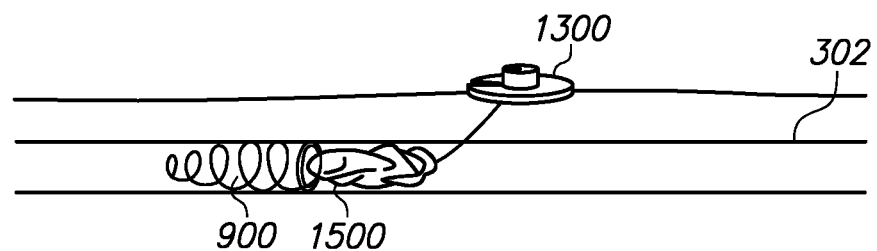
FIG. 16 illustrates the blood clot of FIG. 15 trapped by the vascular filter.

FIGS. 15 and 16 illustrate a blood clot 1500 approaching and being captured by the deployed vascular filter. As the blood clot 1500 migrates down the vein, it will encounter and preferably become trapped by the coil 900 of the vascular filter. As illustrated in FIG. 16, the blood clot 1500 will become lodged or entangled with the vascular filter's coils, and, in this way, the clot is prevented from entering other regions of the subject's circulatory system.

In the event that a blood clot 1500 is captured by the vascular filter, the clot may be removed in one of several ways. First, the entangled blood clot 1500 may be verified using ultrasound or x-ray techniques. If there is a blood clot 1500, then the blood clot may be dissolved using anticoagulation therapy or any other means. If the blood clot 1500 does not dissolve in a timely manner, the attending physician may decide to perform additional procedures such as thrombectomy or thrombolysis to resolve the blood clot. In some cases, permanent placement of a standard IVC filter may be required where the blood clot does not dissolve.

Figure 17:
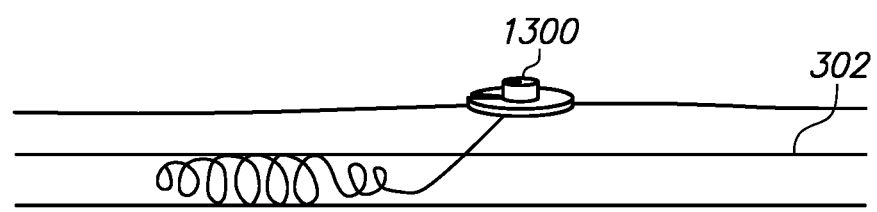
FIGS. 17, 18A, 18B, 18C, 18D, and 19 illustrate removal of the vascular filter.
Figure 18A:
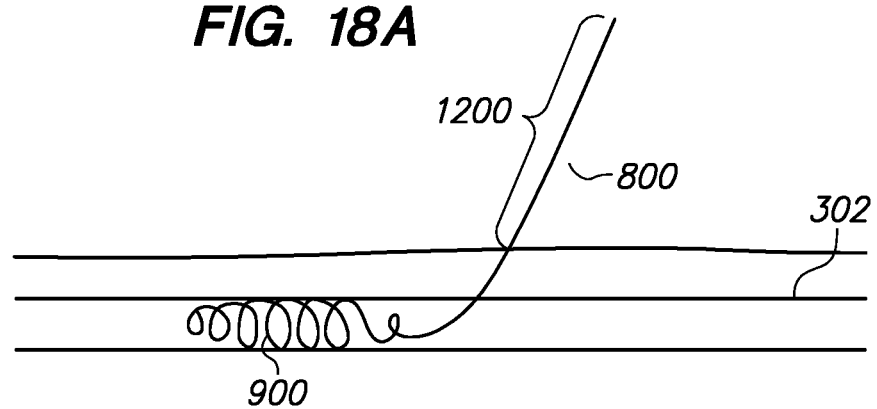
Figure 18B:
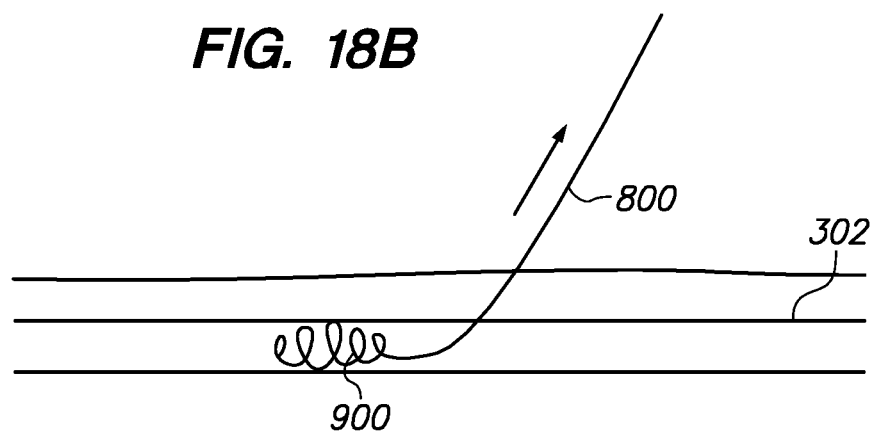
Figure 18C:
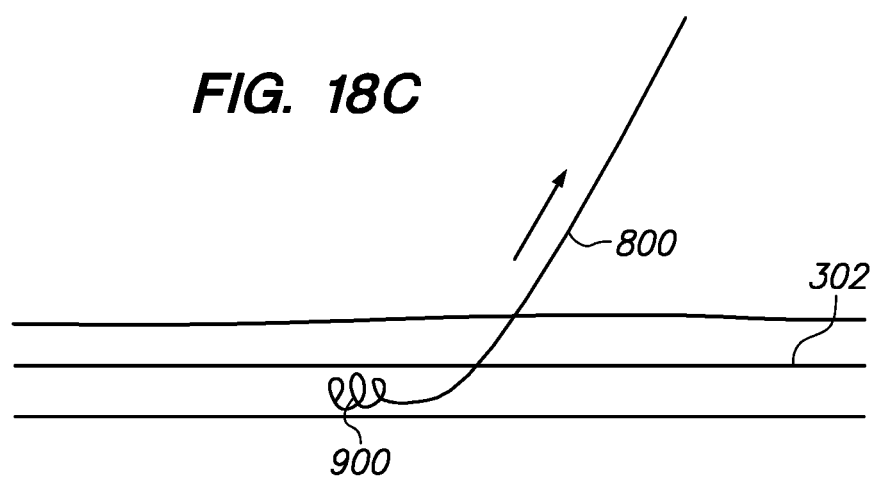
Figure 18D:
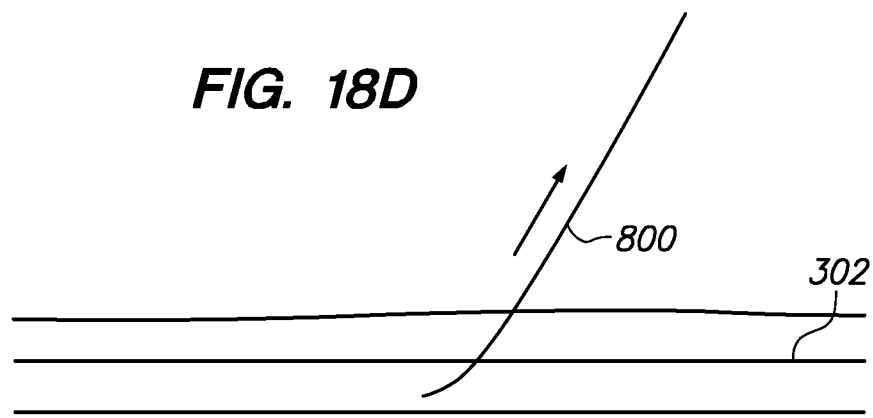
Figure 19:
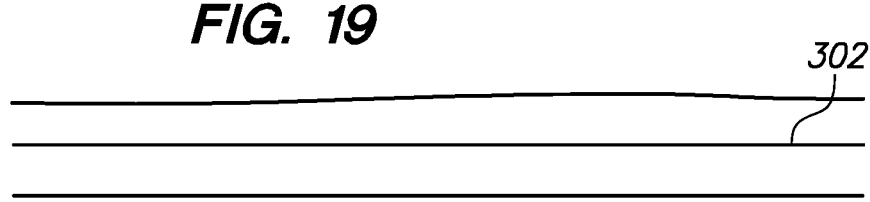

FIGS. 17 through 19 illustrate removal of the vascular filter. In FIG. 17, the fixation device 1300 and associated dressing are removed from the patient's skin surface 1202. Next, the protruding portion 1200 of the filter wire 800 is drawn away from the patient. As the filter wire 800 is drawn out of the patient, the filter coil 900 unwinds and/or unravels as illustrated in FIGS. 18A through 18D. A hydrophilic coating or hydrophilic filter wires 800 may be used, in one or more embodiments, to facilitate removal of the filter coil 900. Once the filter wire 800 is completely extracted from the patient as shown in FIG. 19, the vascular filter has been successfully removed and may be discarded.

The vascular filter disclosed herein has several advantages over known IVC filters. The new vascular filter is inexpensive and easily deployed/removed with minimal intrusion to the patient. In contrast, existing vascular filters require a complex and potentially risky deployment procedure which is very expensive, requires a team of medical professionals and the use of an operating room or cardiology suite. Additionally, existing vascular filters require an even more complicated and risky procedure for removal.

The new vascular filter is placed without the need for complex fluoroscopic guidance (i.e., the new filter may be placed blindly). For example, unlike existing filters that are placed within the inferior vena cava which requires x-ray fluoroscopic guidance for deployment, the new vascular filter may be placed without using any x-ray or imaging equipment.

The new vascular filter is minimally invasive and can be deployed at the patient's bedside or in an emergency room setting. Correspondingly, removal of the new vascular filter may be performed at a convenient location such as bedside.

The new vascular filter reduces the risk of complications because the filter is placed in a more conducive location within the patient's body. As disclosed herein, the new vascular filter may be placed in the pelvic or groin region of the patient unlike existing IVC filters which are generally placed in the upper abdomen or thoracic region. As a result, the new vascular filer is placed within one or both of the more accessible common femoral veins and is minimally intrusive for the patient. Another desirable aspect of the new vascular filter is a substantial reduction in recovery time for either deployment or removal of the new filter. In contrast, the existing filters require a substantial recovery time for both deployment and removal.

As an improvement to the filter and method of use described above, also disclosed is the filter configured as a route for infusion of fluids, gels, or medications through the filter and into the blood stream. The infused material may medicate the entire body or vascular system, or just the area of the filter. As such treatment can be directed to a very direct and focused area of the body or arterial system. As discussed above, the filter may be used to retain clots and as such, while the clot is retained within the filter, medication may be applied or infused through the filter as disclosed below to target the retained clot. This provides the benefit of concentrating the medication to the clot which is particularly useful for application of clot dissolving medication such as, but not limited to, Tissue Pasminogen Activator (TPA—Alteplase). In addition, it is also contemplated that medication may be infused through the filter as described below to prevent clotting of the blood around or onto the filter, or any other type of build-up of material or growth on the filter. This extends the effective life of the filter within the body and increases the ease of removal.

Figure 20:
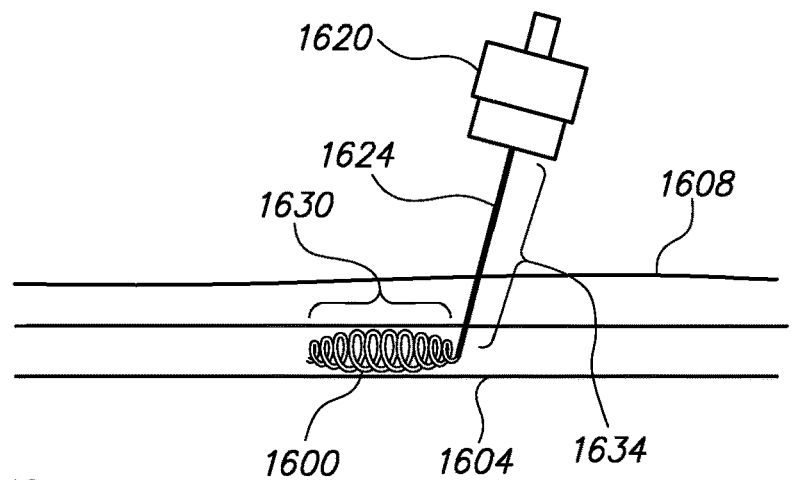
FIG. 20 illustrates an infusible filter and associated hub assembly.

FIG. 20 illustrates an infusible filter and associated hub assembly. As discussed above, the filter 1600 is located within the vascular system, such as vein 1604 located below the surface of the skin 1608. A hub attachment 1620 connects to the externally located end 1624 of the filter 1600. The base function of the filter 1600 operates as described above and in connection with FIGS. 1-19. In this embodiment the filter 1600 including the externally located end 1624 includes an inner passageway that is configured to conduct medication or other material such as a liquid or gel. The passageway may comprise a lumen.

The filter wire maybe categorized into a perforated section 1630 which is contained within in the vascular system. The filter wire also includes an un-perforated section 1634 that connects the perforated section 1630 at a distal end and to the attachment hub at the proximal end. The perforated section has one or more openings (shown in FIG. 21) through which the medication or other material may exit the filter. The number and shape of the openings may be varied to meet the requirements of the filter, medication, and particular medical application.

The filter sections 1630, 1634 includes a passage between an open end at the hub attachment 1620 and the perforations (not shown in FIG. 20) for the movement of the medication or other material into the filter, through the filter, and out of the perforations. The hub attachment 1620, the structure of which is discussed below in connection with FIG. 21, serves several purposes and functions. The hub attachments provides an access port to the internal passage within the filter sections 1630, 1634 to thereby provide an input port for the medication or other material. The hub attachment 1620 also provides a clamping or compression element to open and close the opening into the internal passage of the filter. This controls the flow of medication or other material into and output of the internal passage. The hub attachment 1620 also provides an attachment point and structure to attach a syringe, drip line, medication storage/dispensing device infusion pump, or any other element configured to deliver medication or other material to the filter.

Figure 21A:
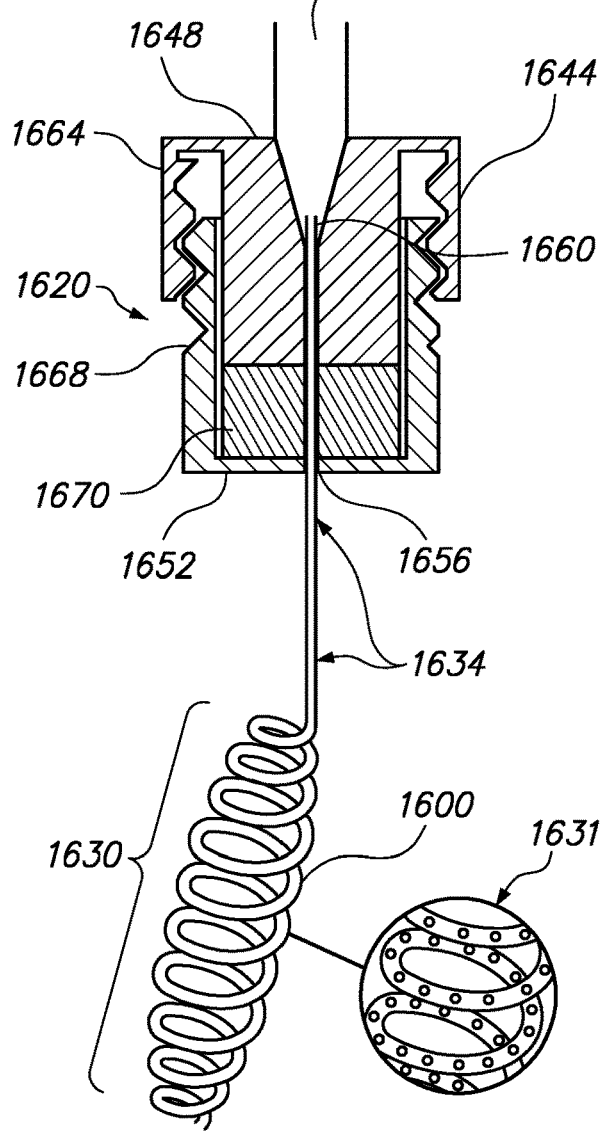
FIG. 21A illustrates a more detailed view of the infusible filter and hub assembly including a close up of the filter wire with infusing mechanism.

FIG. 21A illustrates a more detailed view of the infusible filter and hub assembly including a close up of the filter wire with infusing mechanism. This is but one possible configuration of the filter and hub assembly. It is contemplated that in other embodiments other configurations may be realized without departing from the claims that follow. For example, different medical applications may require that the disclosed and claimed device interface with other medical devices and as such modifications may be made to the device shown without departing from the scope of the invention and claims.

As shown generally, the filter includes hub attachment 1620 and the filter wire 1600. A non-perforated section of the filter wire connects the perforated filter section to the hub assemble. The filter may be made from any type material that is configured to perform as described herein.

A fluid chamber 1640 configured to connect to the hub assembly, which in this embodiment is a luer lock 1644. The fluid chamber 1640 contains medication or other material which is provided to the filter 1600 and ultimately to the patient. The fluid chamber may be part of a syringe, dripline, infusion pump or medication administration device or any other element configured to store and connect to a hub assembly. The fluid chamber 1640 may permanently connect to the filter or may be selectively connectable and removable to apply medication or other material to the filter.

Configured to mate with or connect to the fluid chamber 1640 is a luer lock 1644 having a first end 1648 with an opening configured to mate with the external shape of the fluid chamber 1640, in this embodiment a tapered end. The hub attachment 1620 assembly is an addition to the prior art as it allows wire placement, such as for example, through a needle with the eventual needle removal. Once the entry needle is removed the hub assembly 1620 can be applied to the portion of the filter that is external to the body for infusion.

The luer lock 1644 is generally known in the art and not describe in detail herein. As shown the luer lock 1644 has an internal passageway or lumen from the first end 1648 to a second end 1652. In the second end 1652 is an opening 1656 configured in size and shape to accept a proximal end 1660 of the non-perforated section 1644 filter wire. The opening extends toward the proximal end of the luer lock 1644 to a establish fluid (or there material state) passageway with the fluid chamber 1640. Through this fluid passageway medication or other material may be provided to the filter wire 1600. The medication or other material may be pressurized in the fluid chamber 1640 to establish flow into the lower pressure filter wire. The pressure may be established by a syringe or gravity, or any other force to move the medication or other material from the chamber 1640 to the filter wire.

The luer lock 1644 also includes an outer ring 1664 with internal threaded which rotationally interact with an externally threaded inner frame 1668 of the luer lock. Through rotational movement of the outer ring 1664 relative to the inner frame 1668 the outer ring moves in the linear direction between the proximal end 1648 and the distal end 1652.

The movement of the outer ring 1664 relative to the inner frame 1668 crushes an compression element 1670 that when crushed closes the passage between the chamber 1640 and the internal passageway in the filter 1600. The compression element 1670 may comprise any material capable of performing as described herein. The compression element 1670 is a known structure in the luer lock 1646 and it may also be known to pinch or otherwise close the flow of medication or other material into the filter 1600.

In one configuration the non-perforated section 1634 of the filter in contact with the compression element 1670 may comprise a different material or configuration than the portion of the filter not in contact with the compression element. For example, the non-perforated section 1634 of the filter in contact with the compression element 1670 may be flexible and resilient to return to shape after opening, while the perforated section 1630 may comprise a more stiff material capable of functioning as described above as a filter in a vascular environment.

Figure 21B:
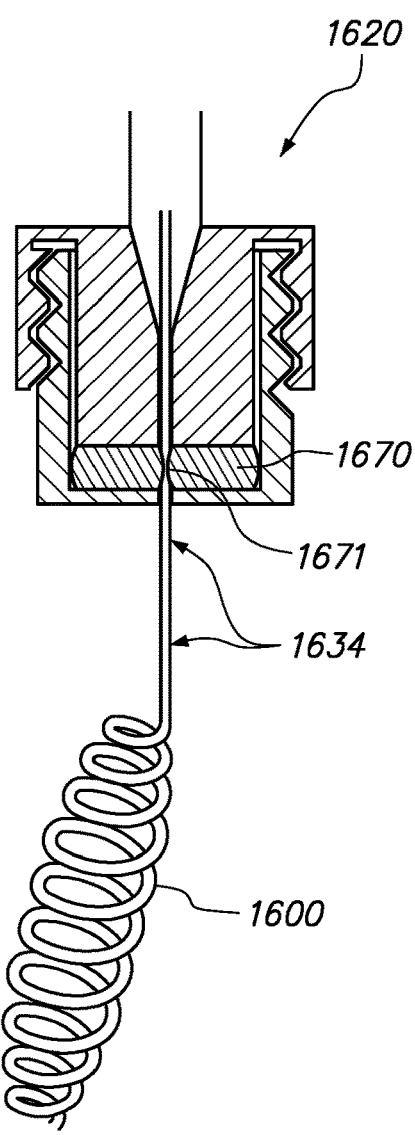
FIG. 21B illustrates the assembly of FIG. 21A with the compression element compressed to close the inner lumen of the view of the filter.

FIG. 21B illustrates the assembly of FIG. 21A with the compression element compressed to close the inner lumen of the view of the filter. As shown the outer ring 1664 is twisted relative to the inner frame 1668 to compress (shown at element 1671) the compression element 1670, which in turn compresses the inner passageway or lumen to stop the flow of medication or other material.

Figure 22:
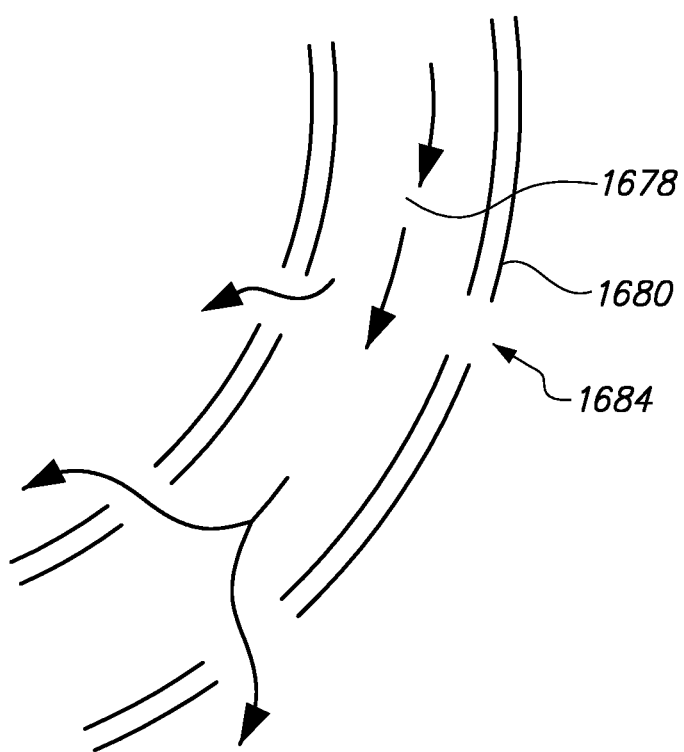
FIG. 22 illustrates a close up view of the perforated section of filter wire with medication outflow holes.

Also shown in FIG. 21A is a close up view 1631 of the perforated section 1630 of the filter. Each of the dots in the coiled filter wire comprise opening or holes through which the medication or other material may pass into the blood steam FIG. 22 illustrates a more detailed version of the filter. As shown the perforated section 1630 of the filter includes an outer wall 1680 which forms an inner passage 1678 or lumen through which medication or other material may flow or be placed. Perforating through the wall 1680 are openings 1684 which provide passages for the medication or other material to exit the inner passageway 1678 or lumen and enter the bloodstream. The openings 1684, which may referred to herein as infusion pores or diffusion pores, may be of any various size and shape and such size and shape may depend on the medication or other material, dosing requirements, patient condition or numerous other factors.

This current improvement allows the place filter to be a route of infusion for fluids and/or medication. The enhanced filter with infusion capabilities can therefore aid in patient care as an extra source of venous access, provides an additional means to protect the filter itself from developing blood clots and potentially will provide a means of breaking up or dissolving the trapped clot via infusion of clot dissolving medications including but not limited to Tissue Plasminoge Activater (TPA) and any other medication now existing or develop in the future.

In summary, once the filter has been placed medication can be infused directly into the blood stream via the inner lumen and multiple infusion pores (openings) located on the intravenous portion of the filter wire. In order to channel fluid through the inner lumen of the filter coil a custom coupling apparatus is provided to attach to a syringe or other device configured to present the medication into the inner passage of the filter wire. The coupler, such as hub assembly, allows for the filter wire with the open inner lumen to be put into fluid communication with a standard IV drip system or other medication administration mechanism via a luer lock connection (hub assembly). Within the coupler is a compression seal (4). When the two coupler bodies are threaded together the compression seal is deformed thus creating a fluid tight seal around the filter wire. Once a seal is made the coupler can be connected to an IV line allowing fluid to pass through the filter wire and infuse into the patient's blood stream.

It is further contemplated that various coatings can be added to the surface of the filter to enhance its biocompatibility or prevent/inhibit growth or development of unwanted surface tissue by the body on the filter. An example is an antithrombogenic antiplatelet coating or material to prevent development thrombi in vitro. This may further prevent or reduce development of clots or scar tissue development on the vascular filter.

Figure 23:
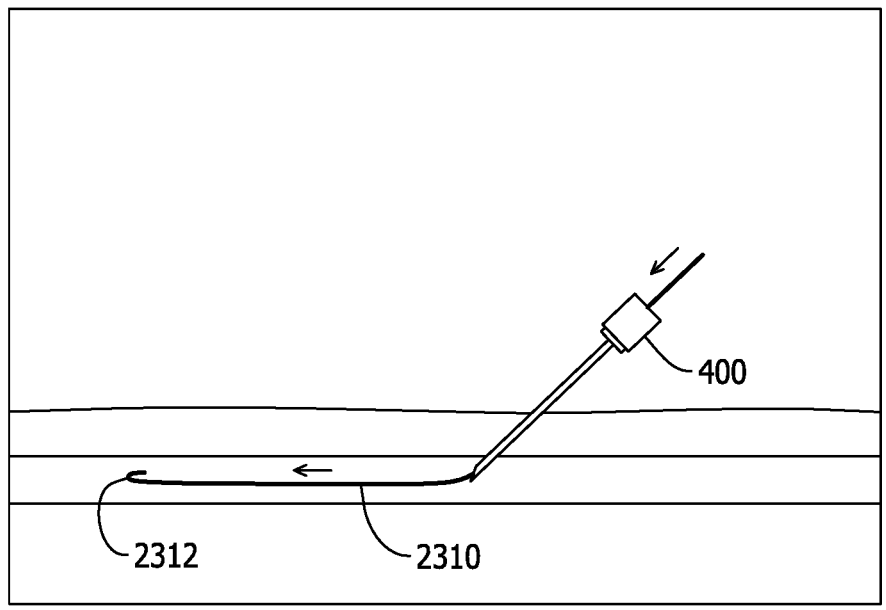
FIGS. 23 and 24 illustrate the deployment of a guidewire into the common femoral vein.
Figure 24:
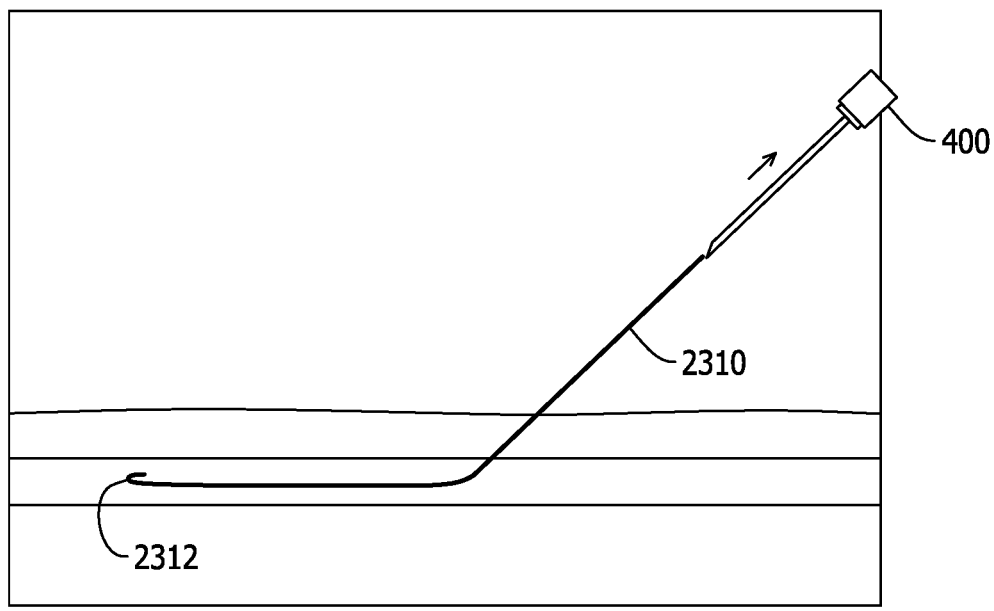

The above-described vascular filters may also be inserted and removed by other methods. In FIG. 23, the needle 400 is inserted into a patient's vein, such as the common femoral vein. A guidewire 2310 is inserted through the needle 400 into the vein. The guidewire 2310 may have a curved tip 2312, such as a u-shaped or a j-shaped tip to facilitate navigation of the guidewire 2310 through the vein and to prevent catching of the guidewire on the vein. The guidewire 2310 may be stored on a reel or other storage device, or inserted as a length of wire. When the guidewire 2310 is deployed in the vein, the needle 400 may be removed as shown in FIG. 24.

Figure 25:
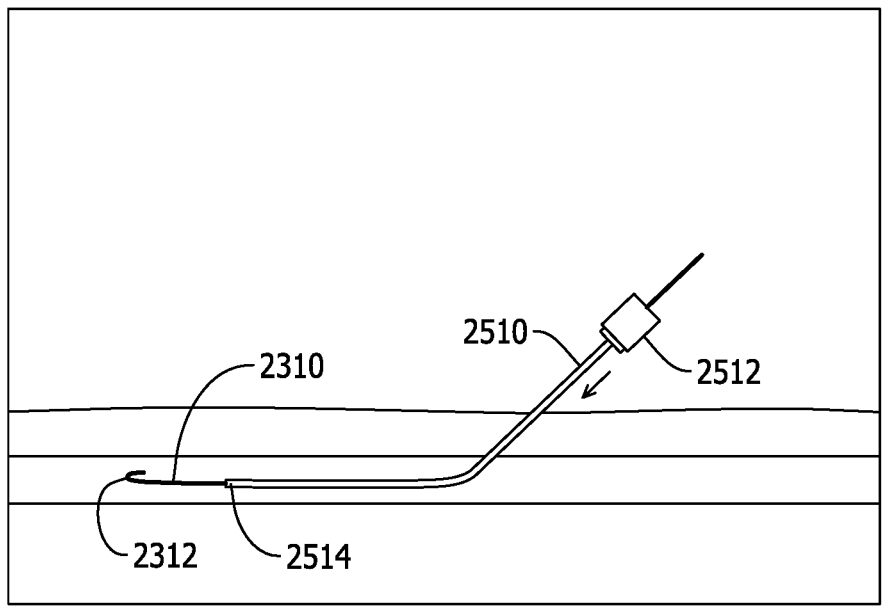
FIG. 25 illustrates the deployment of a catheter along the guidewire.
Figure 26:
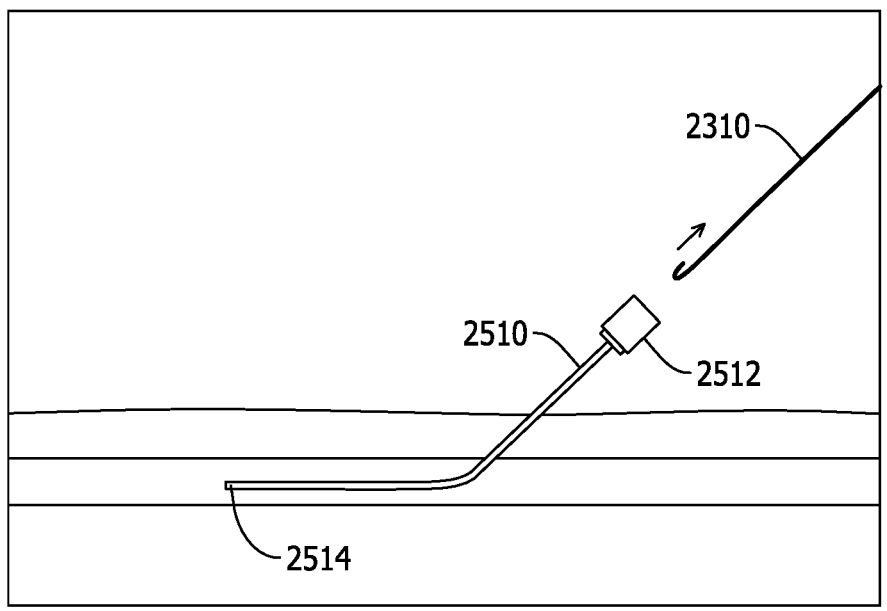
FIG. 26 illustrates the removal of the guidewire.

In addition and in reference to FIG. 25, the guidewire may also be used to establish a sheath or catheter 2510 in a patient. As shown, a sheath or catheter 2510 is utilized to deploy the vascular filter, as will be described in more detail below. The catheter 2510 has a proximal end 2512 and a distal end 2514. A proximal end of the guidewire 2310 outside of the patient is inserted into the distal end 2514 of the catheter 2510, and the catheter is guided over the guidewire 2310 to be inserted into the patient. In this manner, the catheter 2510 is inserted into the patient's vein at a predetermined location along the guidewire 2310. The guidewire 2310 acts as a guide for the catheter. Once the catheter 2510 is properly placed within the vein, the guidewire 2310 is removed by pulling the guidewire 2310 out from the proximal end 2512 of the catheter 2510 as shown in FIG. 26. It is also contemplated that the guidewire 2510 may be left in place to facilitate filter removal, or for other medical procedures.

Figure 27:
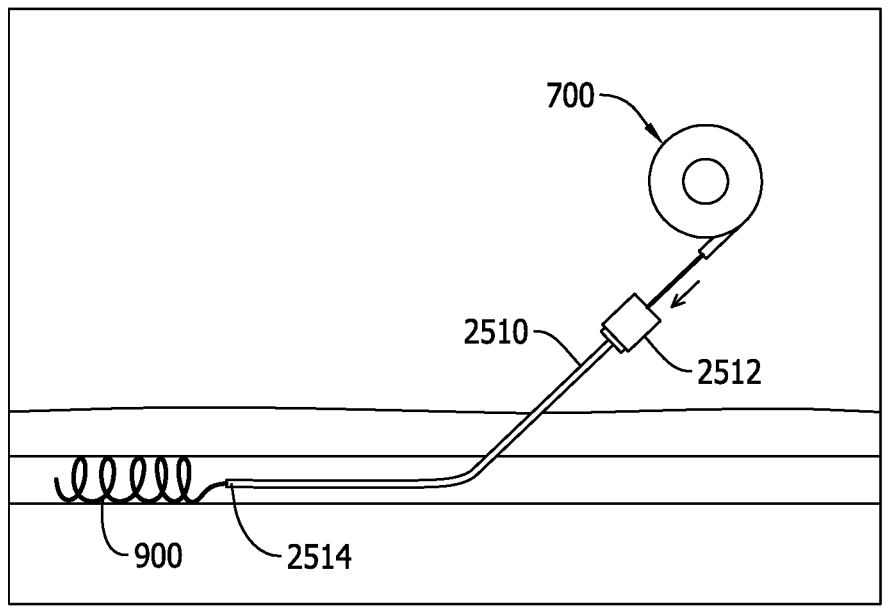
FIG. 27 illustrates the deployment of the vascular filter.

With the catheter 2510 in place, the filter may be inserted in a manner similar as explained with reference to FIGS. 7-11 above. That is, as shown in FIG. 27, a filter dispenser 700 may connect with and insert a distal end of the filter 900 into the proximal end 2512 of the catheter 2510. When the filter 900 exits the distal end 2514 of the catheter 2510, residual stresses in the filter 900 cause the filter wire to coil and form the filter within the patient's vein. In other embodiments deployment in a manner other than coiling may occur.

Figure 28:
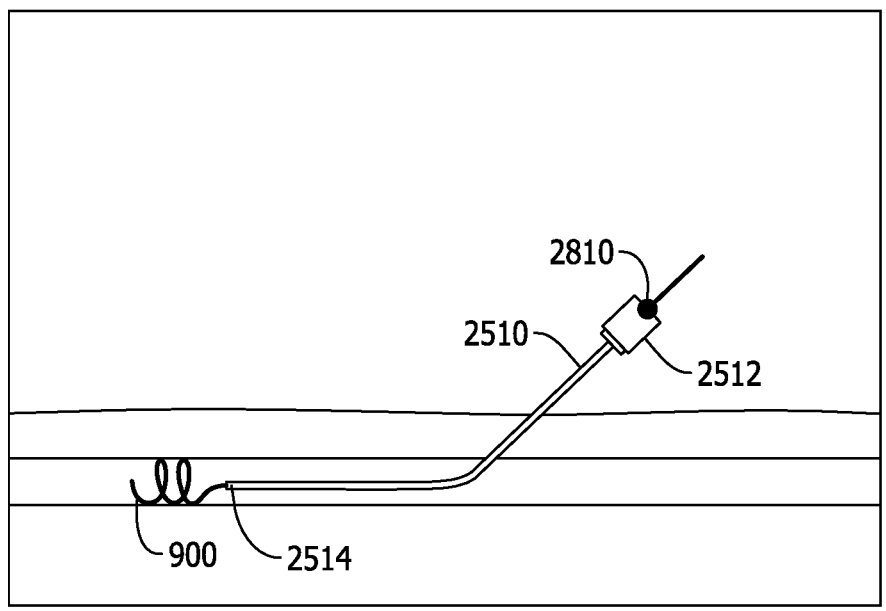
FIG. 28 illustrates the retention of the filter wire in the patient's leg.

In FIG. 28, the proximal end of the catheter 2510 (or sheath) is configured with a valve or seal on or in the exposed end that allows the filter wire (or guide wire) to be placed and advanced/withdrawn without allowing air into the catheter or blood from escaping from the catheter. In this configuration, a "plug" may be mainly used to prevent the wire from advancing further into the vein. This plug may be referred to as a "wire fixation clamp or plug". In another embodiment, the catheter 2510 is plugged by a fixation plug 2810 or any other device or element such as tape, adhesive, ring/loop or the like. The fixation plug 2810 holds the filter 900 in position with respect to the inserted catheter 2510 and may prevent infection while the filter 900 is in place. The catheter 2510 may be plugged with the fixation plug 2810 or other element to prevent blood flow from the catheter.

Figure 29:
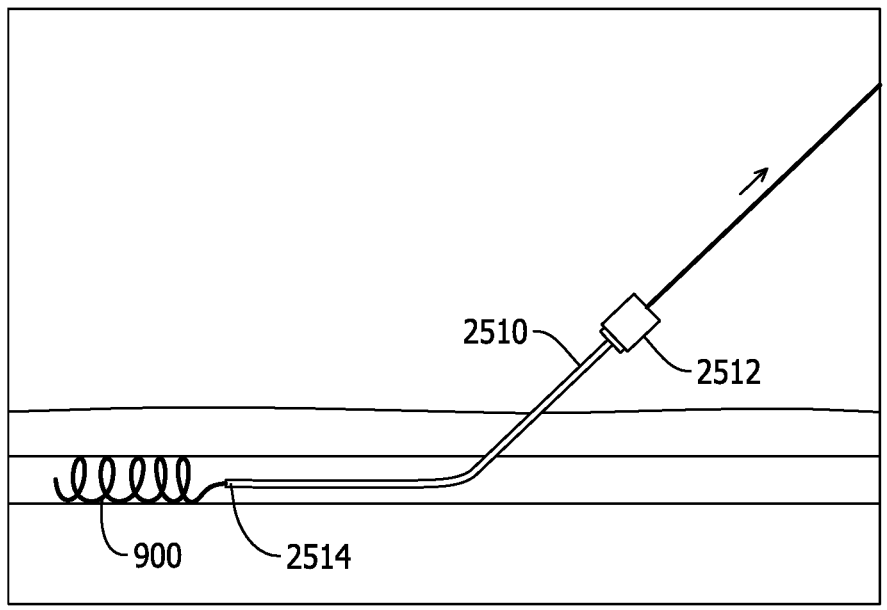
FIG. 29 illustrates the removal of the vascular filter.
Figure 30:
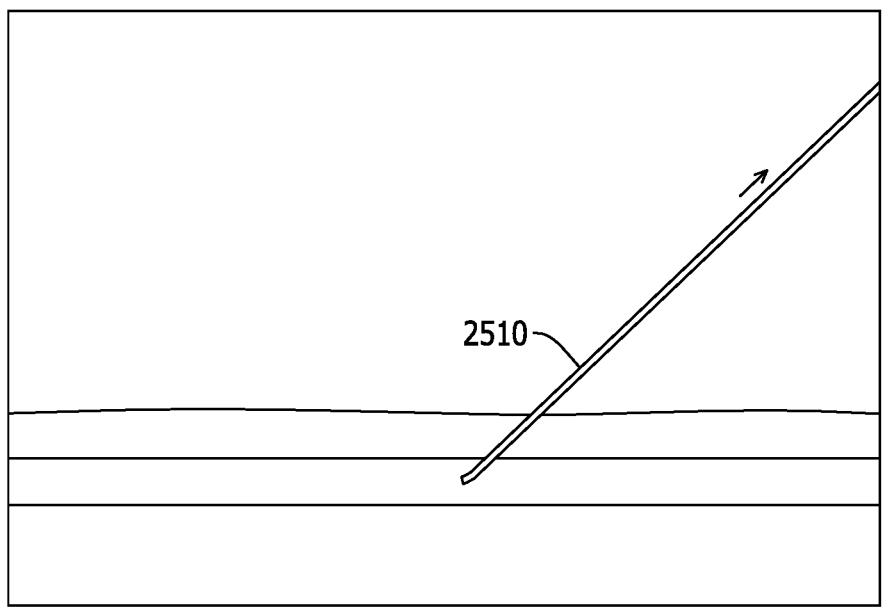
FIG. 30 illustrates the removal of the catheter.

Removal of the filter is shown in FIGS. 29 and 30. Here, the filter 900 is removed by pulling the filter 900 through the catheter 2510 and out of the proximal end 2512 of the catheter. Once the filter 900 is removed, the catheter 2510 is then removed. In this embodiment, the filter 900 may be safely and easily removed by way of the catheter 2510 inserted in the patient. This is due to the pulling force on the filter 900 to be substantially parallel to the vein with the filter is removed through the catheter 2510. The catheter 2510 also protects the skin and vein by providing a protective wall between the filter 900 and the skin and vein. It is contemplated that this system may be used with any type filter such as a filter having an interior passage and outlets for medication disbursement. The filter 900 may also be of any shape and having one or more barbs or rough surfaces to catch the edge of the vein. The filter 900 material may also be smooth to prevent adhesion to the veins.

Figure 31:
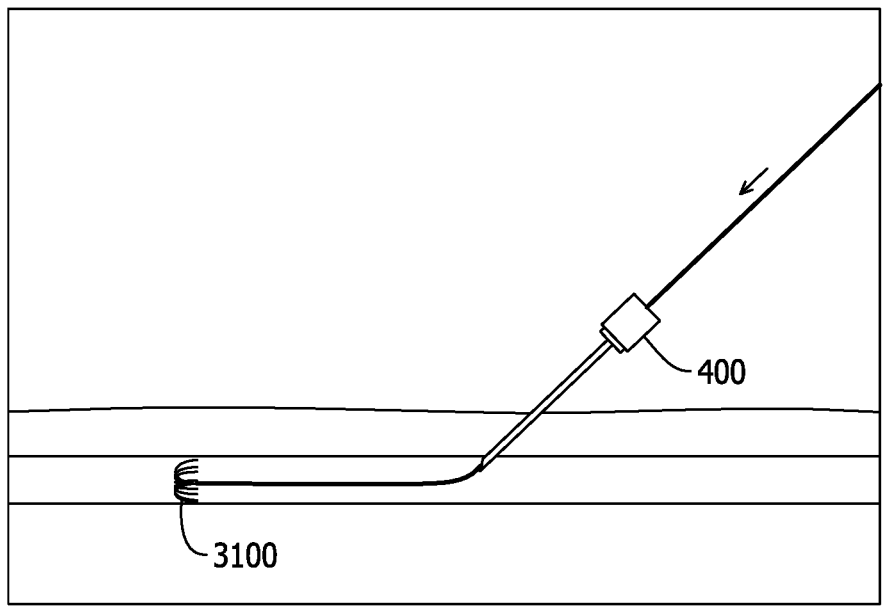
FIG. 31 illustrates the deployment of a vascular filter according to a further exemplary embodiment.
Figure 32:
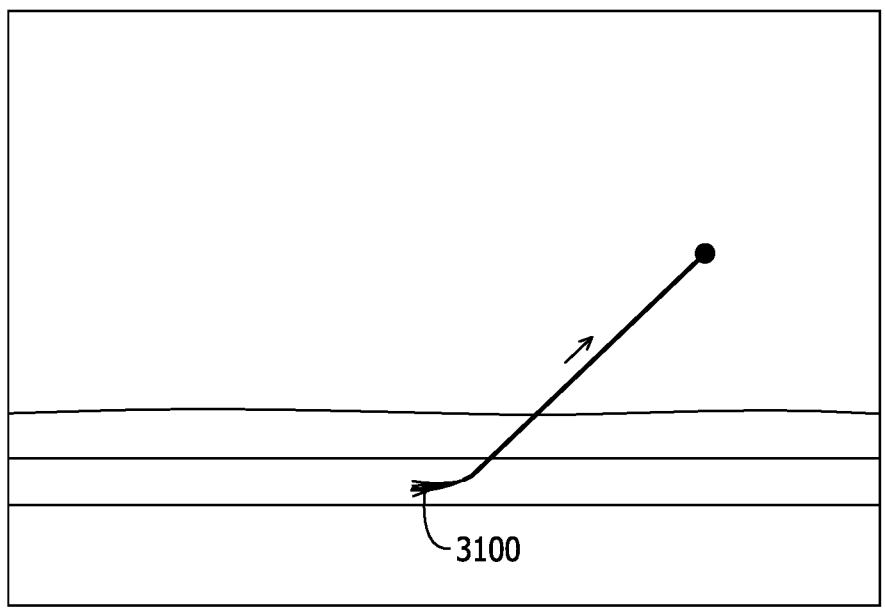
FIGS. 32 and 33 illustrate the removal of the vascular filter shown in FIG. 31.
Figure 33:
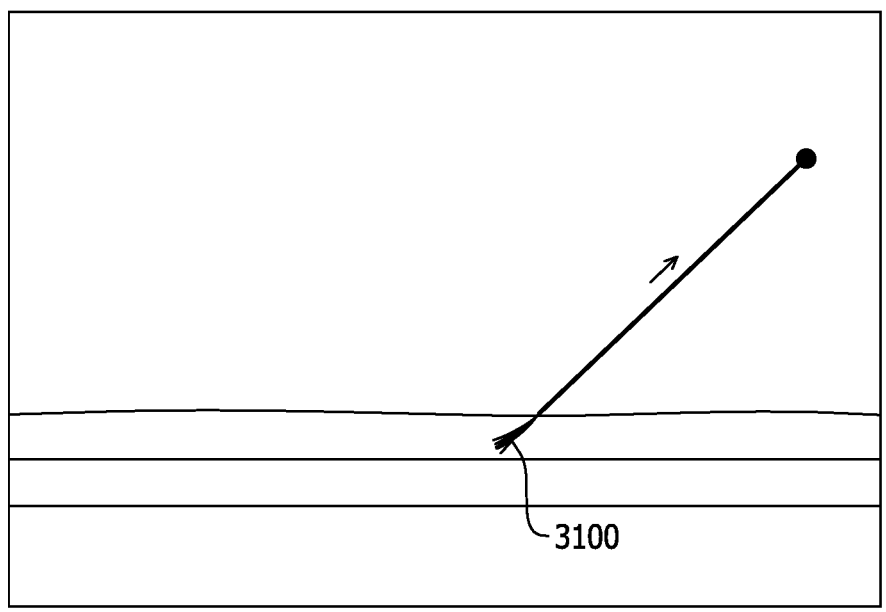

Further modifications may be made within the scope of the invention. For example, as shown in FIG. 31, the filter may be configured to have an "umbrella" end 3100. That is, the end of the filter may be split into several different threads. The filter may deploy from the needle or catheter. The residual stresses within the threads of the umbrella end expand the threads into the umbrella shape 3100 once deployed from the needle 400 (a catheter such as catheter 2510 may also be used). The threads of the umbrella filter 3100 are formed to be flexible such that when the filter is removed, as shown in FIG. 32, the threads flex back and allow easy removal from the vein. It also contemplated that for removal, a flexible sheath may be inserted through a placement needle until the sheath contacts the umbrella portion of the filter causing the threads of the umbrella to collapse backwards and into the sheath for removal from the vessel. Although discussed for use in vein, it is contemplated that the filters may be used in any type or location of blood vessel.

Figure 34:
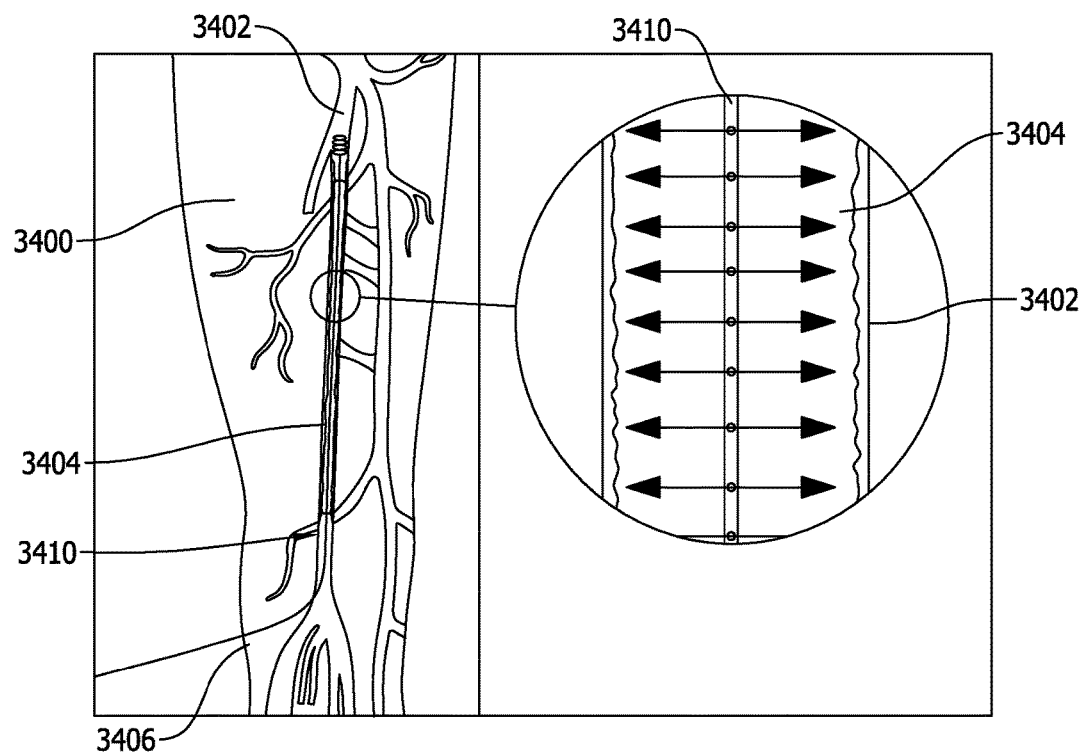
FIG. 34 shows an infusion filter placed in the leg for treatment, according to one embodiment.

FIG. 34 shows an infusion filter placed in the leg for treatment, according to one embodiment. In FIG. 34, a leg 3400 of a patient is shown that has a clot 3404 within a vein 3404. Such clots 3404 may extend a substantial length through the vein 3402 as shown. One method of treating clots 3404 is via thrombolysis, as previously explained. In this embodiment, a new infusion filter 3410 is provided to perform the thrombolysis to remove the clot, as will be explained in more detail below.

Figure 35:
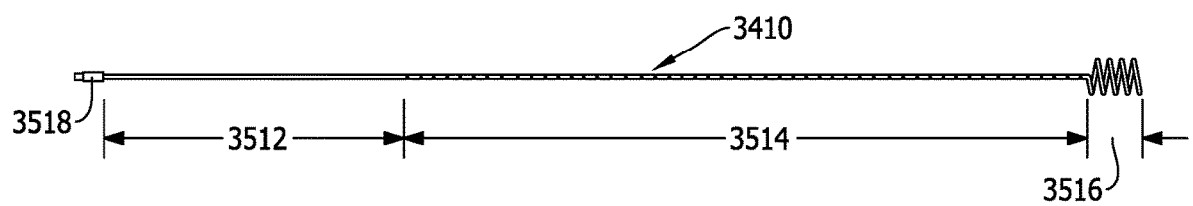
FIG. 35 shows an infusion filter design, according to one embodiment.

FIG. 35 shows an infusion filter design, according to one embodiment. It should be noted that the infusion filter design is not shown to scale, but rather the features are shown to aid in understanding. The relative lengths and sizes of the features in the filter design may vary. In FIG. 35, an infusion filter 3410 comprises a wire with a first proximal length 3512. The first proximal length 3512 is comprised of a hollow inner lumen for fluid transfer with solid circumferential outer wall which is non-permeable. Distally from the first proximal length 3512 is an infusion portion 3514 of the wire that is composed of a permeable outer wall. In one embodiment, the infusion portion 3514 may be formed to have a plurality of holes manufactured therein. Other methods to produce the infusion portion 3514 of the wire 3410 may also be used.

Figure 36A:
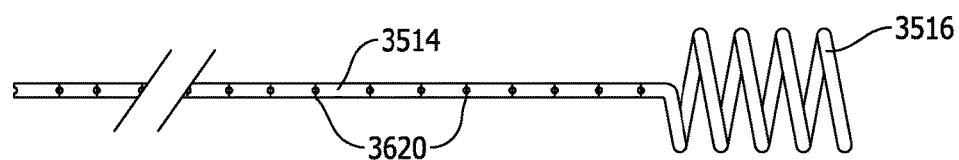
FIG. 36A shows an enlarged distal end of an infusion filter design.
Figure 36B:
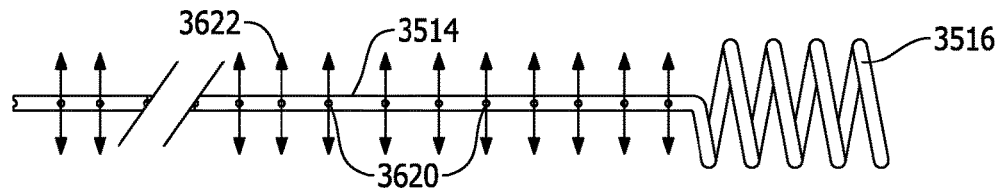
FIG. 36B shows medicine infusion from the enlarged distal end shown in FIG. 36A, according to one embodiment.

FIG. 36A shows an enlarged distal end of an infusion filter design, and FIG. 36B shows medicine infusion from the enlarged distal end shown in FIG. 36A, according to one embodiment. As shown in FIG. 36A, the infusion portion 3514 may comprise several manufactured holes 3620. The holes 3620 may be manufactured via punching, penetrating, or molding the infusion portion 3514, among other methods. Alternately, the infusion portion 3514 may be designed with as woven techniques or materials that are fabricated with micro pores, as well as other means. In FIG. 36B, medication or other fluids 3622 is shown leaving the infusion portion 3514 via the holes 3620. In this manner, medication or fluid may be transported to a specific location in a vein or other blood vessel.

Returning to FIG. 35, the infusion filter 3410 further comprises a filter portion 3516 of the wire at a distal end of the infusion filter 3410. The filter portion 3410 can be configured into a helix shape, a vortex shape, a nested shape, a tangled web shape, or any other suitable filter shape and can be either porous or non-porous depending on the materials used and their configuration. Similar to the filters described above, the filter portion 3516 is configured with residual stresses or surface tensions such that the filter 3516 takes shape once deployed from a sheath or catheter within a blood vessel.

On the proximal end of the filter 3410, a luer lock type adaptor 3518 is employed that can be attached to a syringe or medical tubing for medication infusion. The luer lock adapter may be either prefixed to the wire or may be an attachment that is attached to the infusion wire. For example, the infusion wire may be advanced into the vessel to the desired location and then the luer lock attached to add an infusing capability.

Figure 37:
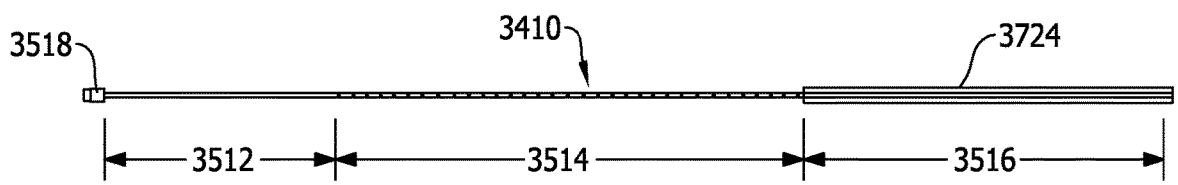
FIG. 37 shows a device for placing an infusion filter, according to one exemplary embodiment.

As shown in FIG. 34, the filter 3410 is inserted into the vein 3402 from an access point around the knee area 3406 of the leg 3400. The filter 3410 is then inserted through the clot 3404 so that the filter portion 3516 can be deployed downstream in the vein 3402 from the clot 3404. FIG. 37 shows a device for placing an infusion filter, according to one exemplary embodiment. An infusion device specific for wires such as a Tuohy-Borst Adapter may be used. In FIG. 37, a configuration for deployment is illustrated where the filter portion 3516 of the infusion filter wire 3410 is loaded in a straight configuration within an outer cover 3724. The filter portion 3516 is deployed when advanced through a catheter or sheath by inserting the outer cover 3724 into the opening of a catheter or sheath then advancing the filter wire 3410 through the vein until it is at the desired location. The filter portion 3516 is then advanced out of the outer cover 3724 until the filter portion 3516 assumes it neutral coiled or previously preconfigured design. The outer cover 3724 is then removed by way of a peel-away design commonly used in the field. In other embodiments, the filter wire 3410 can be configured with or without the luer lock 3518 and can be connected directly for infusion using a Tuohy Borst infusion connector. In this configuration the deployment cover, catheter or sheath can be removed without need for peal-away design.

Figure 38A:
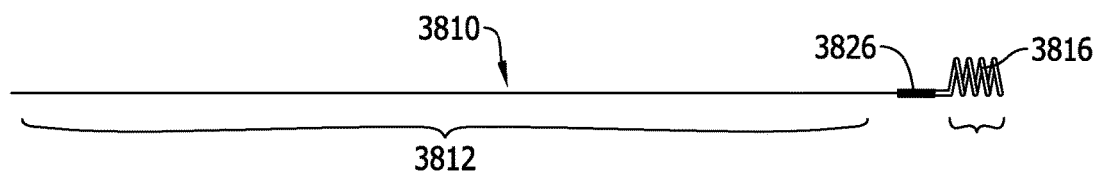
FIG. 38A shows a wire and filter for a system for performing thrombolysis.
Figure 38B:
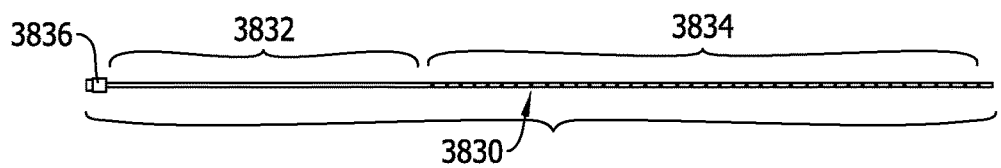
FIG. 38B shows a catheter for the system for performing thrombolysis.
Figure 38C:
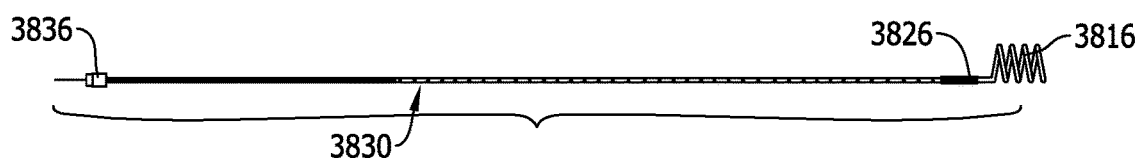
FIG. 38C shows the combination of the wire and catheter of FIGS. 38A and 38B, according to one embodiment.

FIG. 38A shows a wire and filter for a system for performing thrombolysis, FIG. 38B shows a catheter for the system for performing thrombolysis, and FIG. 38C shows the combination of the wire and catheter of FIGS. 38A and 38B, according to one embodiment. It should be noted that the wire and catheter described below are not shown to scale, but rather the features are shown to aid in understanding. In FIG. 38A, a filter wire 3810 is provided with a filter portion 3816 at a distal end of a wire extension portion 3812. The wire extension portion extends through the access point of the patient and into the blood vessel to deploy the filter portion 3816 at the desired location. The filter wire 3810 comprises a stopper 3826 proximal to the filter portion 3816.

The wire 3810 is configured to be deployed within the vein as described in other embodiments above.

As shown in FIG. 38B, an infusion catheter 3830 is also provided. The catheter 3830 comprises a luer lock type device 3836 on a proximal end to which tubing or other equipment may be attached to dispense medicine or fluid into the catheter. The catheter 3830 further comprises a non-infusible length 3832 extending distally from the luer lock device 3836. The non-infusible length 3832 is configured to extend through the incision in a patient and extend into the vein of the patient and includes an interior lumen to transport a fluid. An infusible length 3834 extends distally from the non-infusible length 3832. The infusible length 3834 may comprise several holes or may be constructed to be otherwise permeable such that a fluid or medication flowing from the non-infusible length 3832 is conveyed from the interior lumen of the infusible length 3835 to the outside of the infusible length 3835.

As shown in FIG. 38C, when the catheter 3830 and the filter wire 3810 are deployed, the catheter 3830 extends over and covers the filter wire 3810 up to the stopper 3826. The stopper 3826 is configured to block the flow of fluid from within the lumen of the catheter 3830 such that the fluid is forced to flow through the holes (or other permeable construction) of the infusion length 3834 of the catheter 3830 and into the blood vessel. The stopper 3862 may be omitted in some embodiments where the distal tip of the catheter 3830 is configured with a small valve (such as for example a distal end flow valve) which creates a seal around the wire 3810. This allows infusion with a bare wire extending beyond the tip while still creating a seal in which pressure can develop in the catheter to infusion of medication or other substance into the bloodstream can occur.

Figure 39:
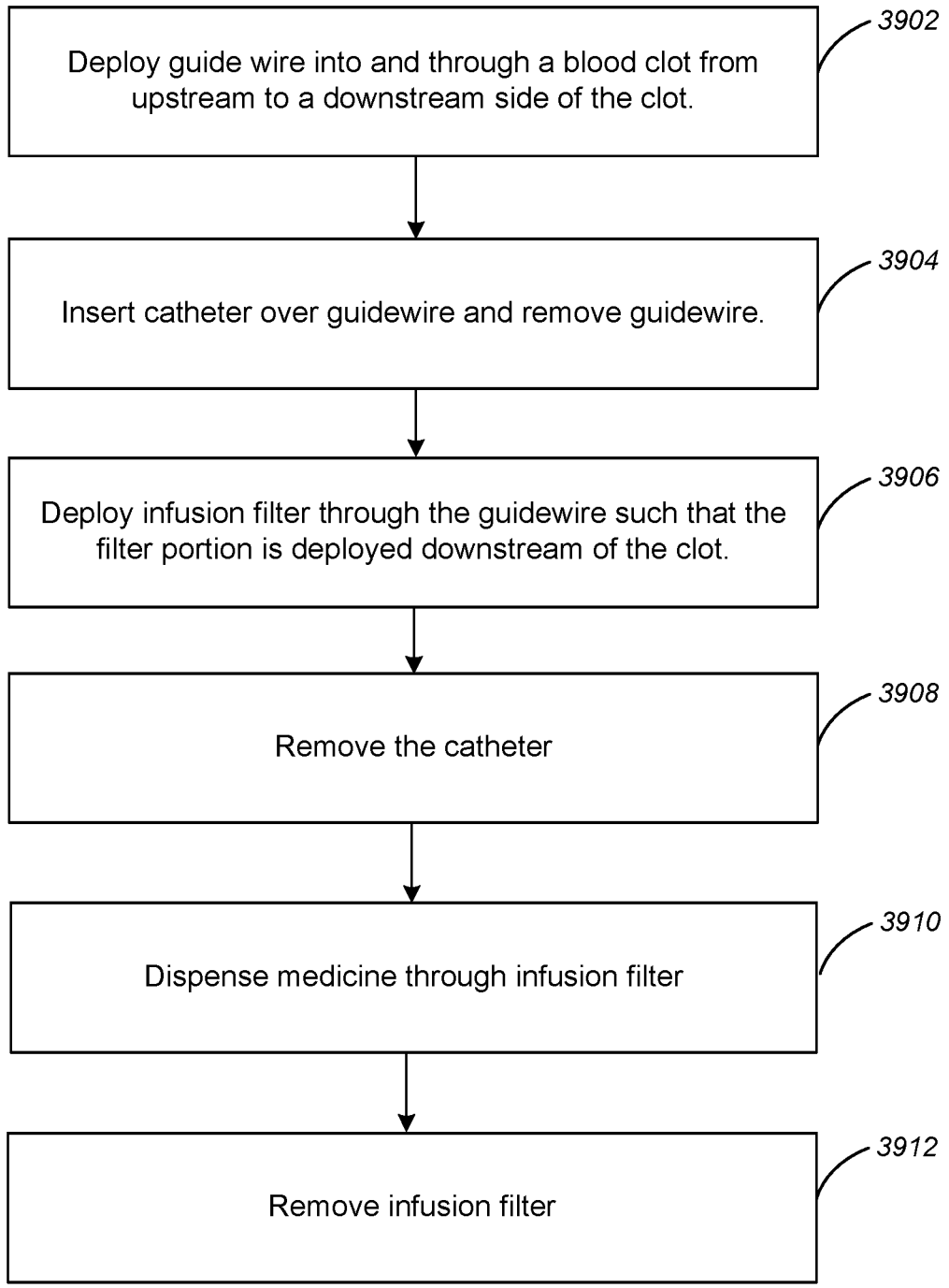
FIG. 39 shows a method for performing thrombolysis, according to an exemplary embodiment.

FIG. 39 shows a method for performing venous thrombolysis, according to an exemplary embodiment. In step 3902, a medical professional deploys a guide wire into and through a blood clot of a patient. For example, as shown in FIG. 34, a patient may have a blood clot 3404 in an upper leg 3400 that extends through a vein 3402 in the upper leg 3400. The guide wire is inserted into the vein upstream from the clot and is directed completely through the clot until a distal end of the guidewire reaches a downstream side of the clot. Once the guidewire is positioned, a catheter is inserted over the guidewire, as described in step 3904. With catheter in position, the guide wire may then be removed.

In step 3906, an infusion filter, such as the one described above, is deployed through the catheter. The infusion filter is positioned so that the filter portion of the infusion filter is deployed downstream in the blood vessel from the clot. Once the infusion filter is in position, the catheter may be removed as described in step 3908. The infusion filter is deployed such that the infusion portion aligns with the blood clot in the patient's blood vessel. When the infusion filter is in place, medication or other fluid may be pumped into the infusion filter and forced through the infusion portion of the filter in step 3910.

For the exemplary thrombolysis method described here, a thrombolytic agent such as those known in the art is fed through the infusion filter into the infusion portion to treat the blood clot by dissolving the blood clot. The infusion filter allows the thrombolytic agent to be directed along the length of the blood clot to help dissolve the blood clot. Furthermore, with the filter portion being disposed downstream from the blood clot, any pieces of the dissolving clot that might break away are filtered and prevented from traveling to other areas of the body where they might cause significant injury or death, such as via a pulmonary embolism. Pieces of the clot caught in the filter may then be gradually dissolved from the medication dispensed through the infusion portion. In some embodiments, the filter portion may also be permeable as described above such that the thrombolytic agent is dispense directly to any clot pieces caught in the filter.

The fluid is dispensed through the infusion filter for a period of time as prescribed by the medical professional. For example, the treatment may last two days. In step 3912, the infusion filter may be removed once the treatment is complete. The infusion filter is removed similar to the removal of the filters described above. The filter portion of the infusion filter is designed with pitch angles and materials such that the filter can be pulled back out through the incision.

The infusion filter and method for performing thrombolysis described above have a number of advantages. First, as compared to prior systems where a filter is deployed by a separate procedure, usually by accessing the jugular vein and guiding the filter through the body to be deployed on the downstream side of the clot in the interior vena cava, the present embodiments allow the filter to be easily placed from an access point upstream from the clot. Further, the infusion filter dispenses the medication, such as the thrombolytic agent, directly at the site of and throughout the length of the blood clot. This allows a total amount of medication delivered to dissolve the clot to be decreased. When the amount of medication is decreased, the safety of the procedure is increased because the risk for the thrombolytic agent to cause damage elsewhere (such creating internal bleeding) is decreased. The safety is also increased due to effective filtering of the vein downstream from the clot. When the clot dissolves from the thrombolytic agent, any large pieces of the clot are filtered and dissolved rather than entering the bloodstream and possibly resulting in a pulmonary embolism or the like. Finally, when the treatment is complete, the filter may be immediately removed without a separate complicated procedure to retrieve the filter.

Other variations of the above described method may also be used. For example, instead of the infusion filter, a filter and infusion catheter may also be used, such as the ones described with reference to FIGS. 38A-38C. The filter portion of the infusion filter might also be deployed via a sheath and a filter cover, as described with reference to FIG. 37. Other modification or combinations with any other embodiments described herein may also be utilized.

While various embodiments of the invention have been described, it will be apparent to those of ordinary skill in the art that many more embodiments and implementations are possible that are within the scope of this invention. In addition, the various features, elements, and embodiments described herein may be claimed or combined in any configuration or arrangement.

What is claimed is:

1. A method for performing venous thrombolysis comprising:
deploying a guidewire within a blood vessel from an upstream side of a blood clot so that a distal end of the guidewire reaches a downstream side of the blood clot;
inserting a catheter over the guidewire;
removing the guidewire while the catheter is in place;
deploying an infusion filter through the catheter, the infusion filter comprising:
a non-infusible length wire extending from a proximal end of the infusion filter, the non-infusible length comprising a lumen extending therethrough;

an infusible length wire extending distally from the non-infusible length wire, the infusible length wire comprising a lumen extending therethrough and a permeable wall having a plurality of holes through which medication may pass; and a filter portion extending from the infusible length wire, the filter portion comprising residual stresses, surface tensions, or both that cause the filter portion to form a predetermined shape when deployed in a blood vessel;

positioning the infusion filter such that the infusible length wire is adjacent to the blood clot and the filter portion is disposed downstream from the blood clot;

removing the catheter with infusion filter in place;

dispensing medication into the blood vessel through the permeable wall for a predetermined treatment period; and removing the infusion filter from the patient.

2. The method of claim 1, wherein the predetermined shape comprises one of a helix shape, a vortex shape, a nested shape, and a tangled web shape.

3. The method of claim 1, wherein the infusion filter further comprises an outer cover that is disposed over the filter portion and is removable from the filter portion when the filter portion is deployed.

4. The method of claim 1, wherein the infusion filter further comprises a luer lock on a proximal end thereof to convey the medication to the lumen of the non-infusible length wire.

5. The method of claim 1, wherein the filter portion comprises a lumen and a permeable wall.

* * * * *